US011484702B2

(12) United States Patent
Dascoli et al.

(10) Patent No.: US 11,484,702 B2
(45) Date of Patent: Nov. 1, 2022

(54) ELECTRODE ASSEMBLIES FOR TREATING ADULT AND PEDIATRIC PATIENTS

(71) Applicant: ZOLL Medical Corporation, Chelmsford, MA (US)

(72) Inventors: Melissa M. Dascoli, Wakefield, MA (US); David N. Craige, III, Attleboro, MA (US); Gary A. Freeman, Waltham, MA (US); Ian Durrant, Arlington, MA (US); James Wilson, Norwood, MA (US); Brian Stonecipher, Thousand Oaks, CA (US); George Reilly, Chelmsford, MA (US); Deborah T. Jones, Dartmouth, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 18 days.

(21) Appl. No.: 15/440,963

(22) Filed: Feb. 23, 2017

(65) Prior Publication Data

US 2017/0259054 A1 Sep. 14, 2017

Related U.S. Application Data

(60) Provisional application No. 62/300,510, filed on Feb. 26, 2016.

(51) Int. Cl.
*A61N 1/04* (2006.01)
*A61N 1/39* (2006.01)

(52) U.S. Cl.
CPC .......... *A61N 1/046* (2013.01); *A61N 1/0492* (2013.01); *A61N 1/3968* (2013.01)

(58) Field of Classification Search
CPC ..... A61N 1/046; A61N 1/0492; A61N 1/3968
USPC ........................................................ 607/142
See application file for complete search history.

(56) References Cited

U.S. PATENT DOCUMENTS

| 5,951,598 A * | 9/1999 | Bishay ..................... A61B 5/68 600/372 |
| 6,125,298 A | 9/2000 | Olson et al. |
| 6,851,364 B1 * | 2/2005 | Suda ....................... B41N 1/006 101/456 |
| 6,990,373 B2 | 1/2006 | Jayne et al. |
| 7,062,321 B2 | 6/2006 | Lyster et al. |
| D658,297 S | 4/2012 | Powers et al. |
| 9,079,044 B2 | 7/2015 | Powers |
| 2003/0088276 A1 * | 5/2003 | Covey .................. A61N 1/3968 607/5 |
| 2014/0243916 A1 | 8/2014 | Freeman et al. |

(Continued)

*Primary Examiner* — Brian T Gedeon
(74) *Attorney, Agent, or Firm* — Fish & Richardson P.C.

(57) ABSTRACT

This document describes an electrode assembly for use with a defibrillator, the electrode assembly comprising at least one electrode including a first surface that can be affixed to either of a pediatric patient and an adult patient and a second surface, wherein a majority of the second surface includes pictorial instructions related to use of the electrode assembly; and a chest compression sensor attached to the at least one electrode, wherein the at least one electrode is configured to be used on an adult patient when the electrode assembly is in a first orientation, and wherein the at least one electrode is configured to be used on a pediatric patient when the electrode assembly is in a second orientation.

22 Claims, 13 Drawing Sheets

(56) References Cited

U.S. PATENT DOCUMENTS

| | | | |
|---|---|---|---|
| 2014/0274633 A1* | 9/2014 | Tilton | B31B 50/26 493/51 |
| 2015/0094625 A1* | 4/2015 | Freeman | A61N 1/046 601/41 |
| 2016/0082246 A1* | 3/2016 | Piazza | A61N 1/0404 607/5 |
| 2016/0279405 A1* | 9/2016 | Riley | A61N 1/046 |

* cited by examiner

ELECTRODE ASSEMBLIES FOR TREATING ADULT AND PEDIATRIC PATIENTS

CLAIM OF PRIORITY

This application claims priority under 35 USC §119(e) to U.S. Patent Application Ser. No. 62/300,510, filed on Feb. 26, 2016, the entire contents of which are hereby incorporated by reference.

TECHNICAL FIELD

This application relates to the field of adult and pediatric defibrillation and defibrillation equipment.

BACKGROUND

Sudden health problems such as sudden cardiac arrest and injuries caused by accidents result in death and/or permanent injury of thousands of people every year. Fast and competent care to resuscitate such victims of these problems can be essential to positive outcomes in such situations. For example, it is said that the chance of surviving a sudden cardiac arrest falls by ten percent for every minute of delay in providing effective treatment.

Resuscitation treatments for patients suffering from cardiac arrest generally include clearing and opening the patient's airway, providing rescue breathing for the patient, and applying chest compressions to provide blood flow to the victim's heart, brain, and other vital organs. If the patient has a shockable heart rhythm (ventricular fibrillation or pulseless ventricular tachycardia), resuscitation also may include defibrillation therapy.

SUMMARY

This document describes an electrode assembly that can have at least one electrode including a first surface that can be affixed to either of a pediatric patient and an adult patient and a second surface, wherein a majority of the second surface includes pictorial instructions related to use of the electrode assembly; and a chest compression sensor attached to the at least one electrode, wherein the at least one electrode is configured to be used on an adult patient when the electrode assembly is in a first orientation, and wherein the at least one electrode is configured to be used on a pediatric patient when the electrode assembly is in a second orientation.

In some implementations, instructions for use with an adult patient are oriented for readability when the electrode assembly is in the first orientation and wherein instructions for use with a pediatric patient are oriented for readability when the electrode assembly is in the second orientation. In some implementations, the at least one electrode includes a first electrode is configured to be affixed to a chest region of the adult patient when the electrode assembly is in the first orientation, and wherein the first electrode is configured to be affixed to an intercostal region of the pediatric patient when the electrode assembly is in the second orientation. In some implementations, the first electrode is configured to be affixed to an upper right chest of the adult patient when the electrode assembly is in the first orientation, and wherein the first electrode is configured to be affixed to a lower left intercostal region of the pediatric patient when the electrode assembly is in the second orientation. In some implementations, the at least one electrode includes a second electrode configured to be affixed to a lower left intercostal region of the adult patient when the electrode assembly is in the first orientation, and wherein the second electrode is configured to be affixed to a posterior region of the pediatric patient when the electrode assembly is in the second orientation. In some implementations, the pictorial instructions related to use of the electrode assembly include a representation of the at least one electrode affixed to a surface of an adult patient when in the first orientation, and a representation of the at least one electrode affixed to a surface of a pediatric patient when in the second orientation.

In some implementations, the representation of the at least one electrode affixed to a surface of a pediatric patient includes a symbol indicating pediatric use. In some implementations, the representation of the pediatric patient is oriented approximately 180 degrees with respect to the representation of the adult patient on the pictorial instructions. In some implementations, the representation of the pediatric patient is oriented approximately 90 degrees with respect to the representation of the adult patient on the pictorial instructions.

In some implementations, the pictorial instructions related to use of the electrode assembly include a background portion that corresponds with a representation of the at least one electrode provided in the pictorial instructions. In some implementations, the background portion is substantially colored to correspond with the representation of the at least one electrode provided in the pictorial instructions. In some implementations, substantially all of the second surface comprises the pictorial instructions related to use of the electrode assembly.

In some implementations, the second surface comprises polypropylene. In some implementations, the second surface of the at least one electrode includes a dielectric material having the pictorial instructions printed thereon. In some implementations, the polypropylene is fixed to the electrode using a polypropylene adhesive. In some implementations, the first surface is coated with a conductive hydrogel. In some implementations, the polypropylene is biaxially oriented. In some implementations, the second surface comprises a material having properties that enables substantially all of the second surface to include the pictorial instructions. In some implementations, the at least one electrode is detachable from the chest compression sensor.

In some implementations, the electrode assembly can include a notch indicating a location at which the at least one electrode is detachable from the chest compression sensor. In some implementations, the at least one electrode comprises a removable backing adhered to the first surface. In some implementations, a first portion of the removable backing forms a tab that can be gripped by a user and a second portion of the removable backing adheres to the first surface. In some implementations, the tab is substantially free of adhesive material. In some implementations, at least one of the removable backing and the first surface includes at least one indicator comprising instructions for removing the backing from the first surface. In some implementations, the at least one indicator includes a first arrow graphically illustrated on the removable backing and a second arrow graphically illustrated on a second surface of the at least one electrode.

In some implementations, the second surface is located opposite the first surface. In some implementations, the at least one electrode includes coloring that corresponds with coloring of the defibrillator.

In some implementations, the at least one electrode comprises at least one of a rectangular-like and an oval-like shape. In some implementations, the electrode assembly can have a connector to an electronic port of the defibrillator, the connector terminating an electronic cable, wherein the connector is oriented such that, when connected to the defibrillator, the electronic cable tends to wrap over an edge of the defibrillator. In some implementations, the electrode assembly can have a connector to an electronic port of the defibrillator, the connector terminating an electronic cable, wherein the electronic cable extends laterally from the connector substantially parallel to a surface of the defibrillator. In some implementations, the electrode assembly includes a housing for the chest compression sensor, wherein a surface of the housing is marked with a pattern to assist a user in orienting the at least one electrode.

In some implementations, the pattern extends to substantially the perimeter of the surface of the housing of the chest compression sensor. In some implementations, the surface of the housing of the chest compression sensor is marked with pictures of hand placement for performing chest compressions.

A packaging for an electrode assembly can include two sheets of material affixed for at least a portion of their respective outer edges, the two sheets forming an internal pocket for enclosing the electrode assembly; the two sheets of material each having a respective edge that is tapered, the tapered edges each forming tabs that can be gripped by a user.

In some implementations, the packaging includes a compartment formed from translucent or transparent material and sized to fit a pair of scissors that can be used to cut clothing of a patient. In some implementations, the compartment is affixed to an exterior of at least one of the two sheets of material. In some implementations, at least one of the tabs comprises a visual indication of how to separate the two sheets when gripped by the user. In some implementations, the visual indication comprises an arrow. In some implementations, the heat seal forms an angle having a vertex proximate to the tapered edge. In some implementations, the packaging includes a surface including instructions for using the electrode assembly. The instructions for using the electrode assembly can include pictorial instructions including a representation of the two sheets gripped and separated by the user. The instructions for using the electrode assembly can include pictorial instructions including a representation of the electrode assembly affixed to a surface of an adult patient when in a first orientation.

The representation of the electrode assembly in the first orientation includes a first electrode affixed to a chest region of the adult patient and a second electrode affixed to an intercostal region of the adult patient. The instructions for using the electrode assembly has pictorial instructions including a representation of the electrode assembly affixed to a surface of a pediatric patient when in a second orientation. The representation of the electrode assembly in the second orientation includes a first electrode affixed to an intercostal region of the pediatric patient and a second electrode affixed to a posterior region of the pediatric patient. In some implementations, the representation of the electrode assembly in the first orientation includes a symbol indicating pediatric use.

The electrode assembly can include a dielectric material including a first surface adapted to face toward the patient upon placement of the electrode assembly and a second surface adapted to face away from the patient upon placement of the electrode assembly, the second surface of the dielectric material having visual instructions related to use of the electrode assembly printed thereon; a conductive material in contact with the dielectric material; and a conductive gel in contact with the conductive material, wherein the conductive material and the conductive gel are configured to provide a therapeutic shock to the patient upon a determination that the patient requires defibrillation.

In some implementations, the electrode assembly can be configured to be used on an adult patient when the electrode assembly is in a first orientation, and configured to be used on a pediatric patient when the electrode assembly is in a second orientation.

In some implementations, the dielectric material comprises polypropylene. In some implementations, the polypropylene is biaxially oriented. In some implementations, the dielectric material is capable of withstanding voltages of at least 800 V and able to pass a working voltage test according to IEC 601-2-25.

In some implementations, the visual instructions have a print resolution exceeding 50 DPI. In some implementations, the visual instructions have a print resolution of between 50-1500 DPI. In some implementations, a contact angle of the surface of the dielectric material is between 5-85 degrees. In some implementations, the conductive material includes a metallic material. In some implementations, the conductive material includes a polymer-based ink.

In some implementations, the electrode assembly includes at least one electrode including a first electrode configured to be affixed to a chest region of the adult patient when the electrode assembly is in the first orientation, and wherein the first electrode is configured to be affixed to an intercostal region of the pediatric patient when the electrode assembly is in the second orientation. In some implementations, the first electrode is configured to be affixed to an upper right chest of the adult patient when the electrode assembly is in the first orientation, and wherein the first electrode is configured to be affixed to a lower left intercostal region of the pediatric patient when the electrode assembly is in the second orientation. In some implementations, the at least one electrode includes a second electrode configured to be affixed to a lower left intercostal region of the adult patient when the electrode assembly is in the first orientation, and wherein the second electrode is configured to be affixed to a posterior region of the pediatric patient when the electrode assembly is in the second orientation. In some implementations, the visual instructions related to use of the electrode assembly include a representation of the at least one electrode affixed to a surface of an adult patient when in the first orientation, and a representation of the at least one electrode affixed to a surface of a pediatric patient when in the second orientation.

The techniques described herein may have one or more of the following advantages. An electrode assembly, such as those for use with a defibrillator, can have clear instructions printed onto one or more parts or portions of the assembly itself such that a rescuer need not consider external instructions which could be lost or misplaced during treatment. The instructions can be printed in large, colorful pictures such that the rescuer can easily understand. Each piece of the electrode assembly can have a distinguishing color which covers a significant portion of the instructions on the piece of the electrode assembly and distinguishes the piece from the other pieces in the assembly at a glance. These colors can also be used to represent each piece of the electrode assembly in the instructions, aiding the rescuer in interpreting the instructions. For example, the upper surface of one or more electrodes of the electrode assembly facing away from the patient (and toward a rescuer) may include pictorial instructions related to use of the electrode assembly.

Electrode assemblies in accordance with the present disclosure may be used in cooperation with defibrillators and/or monitors for treating a patient. One or more electrodes of an electrode assembly may be configured to transmit a defibrillating shock to a patient. The electrode(s) may further be configured to sense ECG signals arising from the patient. In some embodiments, the electrode(s) may be attached or otherwise coupled to a chest compression sensor, which may be used to assist a user in providing appropriate cardiopulmonary resuscitation (CPR) feedback to the user. Such feedback may include, for example, providing guidance to the user as to how to better perform chest compressions (e.g., rate, depth, release) and/or provide an indication of perfusion performance, amongst others.

The electrode assembly can be used for both adult and pediatric patients. The instructions can be printed on each piece of the electrode assembly such that when the rescuer needs to place and orient each piece on a patient, the instructions will be in the proper orientation for reading them. Thus, when the rescuer orients one or more parts (e.g., electrode pads) of the electrode assembly in order to read or otherwise be guided by the instructions for using the part(s) which are relevant to the current situation (e.g., whether the patient is an adult or child), the part(s) of the electrode assembly will be in the correct orientation for placement on the patient. For example, when placed in a first orientation, an electrode may be configured to be used on an adult patient and, when placed in a second orientation different from the first orientation, the same electrode may be configured to be used on a pediatric patient.

The electrode assembly can be made of materials that allow the electrodes to be thin and conformable to patients of different sizes without tearing or creasing thereof. The electrode assembly may include a dielectric material with an upper surface adapted to face away from the patient upon placement of the electrode assembly, where the upper surface of the dielectric material has visual (e.g., pictorial, graphical) instructions related to use of the electrode assembly printed directly thereon. This configuration may be in contrast to conventional electrodes where a separate label is adhered to the dielectric; such conventional electrodes may be prone to delamination upon bending of the label from the dielectric. Hence, electrodes described herein may be suitably bent, rolled and/or compacted as desired. Further, the electrode assembly can be stored in a smaller, more compact fashion than would otherwise be the case for more conventional electrodes.

The packaging of the electrode assembly can help the rescuer to follow a preferred procedure for treating a patient. For example, instructions which are consistent with the instructions printed on the electrode assembly can be displayed on the exterior of the package. A rescuer can thus anticipate what instructions the electrode assembly may provide even before opening the packaging. In some embodiments, the packaging may include two sheets of material having tapered edges that form tabs that can be comfortably gripped by the user, for easy opening of the packaging and access to the electrode assembly stored therein. In some cases, as discussed herein, the pull tabs may be free of adhesive or otherwise sticky material, which may provide additional comfort in opening the package. For example, in such a configuration, the tabs may be less likely to inadvertently adhere to hands or gloves of the responder. A pouch for scissors can be prominently displayed on the package exterior since a rescuer will need the scissors before the electrode assembly, e.g., to cut off a patient's clothing. This can help guide the rescuer follow the correct procedure and reduce confusion and mingling of the electrode assembly and other contents which may otherwise be packaged. The container holding the scissors can be translucent so that a rescuer can clearly see the scissors.

DETAILED DESCRIPTION

Adult and pediatric patients often require different treatments during defibrillation therapy. For instance, the defibrillating shock for an adult or relatively large sized individual characteristic of an adult will involve a greater amount of energy (e.g., could be approximately 100 Joules greater) than that for a child or comparatively smaller person. An automated external defibrillator (AED) might have numerous settings which can adjust the device to accommodate both adult and pediatric patients. In some cases, a unique electrode assembly might be necessary to treat a pediatric patient. This can be because the electrode assembly which is typically used by adults may be too large or otherwise unsuitable for use with a pediatric or smaller patient. For example, it may be difficult or awkward to place electrodes constructed for adult use on a pediatric patient. In such cases, an AED might come with two separate electrode assemblies to ensure that pediatric patients can be appropriately cared for. Hence, the present disclosure provides for electrode assemblies that may be suitable for defibrillation and/or administration of CPR to both adult and pediatric subjects, eliminating the need for defibrillation devices to provide multiple differently sized treatment electrodes useable for adult or pediatric subjects. In some cases, the placement, orientation, or both of a set of electrodes that can be used on both adult and pediatric may be different for the pediatric patient than for the adult patient. In such cases, where rescuers are often using electrode assemblies for the first time in an emergency situation, various embodiments described herein provide clear instructions to guide rescuer actions as to how to orient the electrodes of the assembly, so as to reduce any confusion that might otherwise arise. Thus, the electrodes (and, in some examples, its packaging) can be designed to increase efficiency and overall response time by a rescuer.

In some examples, an electrode assembly that includes an electrode and optionally a chest compression sensor can be used with either a pediatric patient or an adult patient. The electrode can be used on either type of patient, and can be oriented on an adult in one way and a pediatric patient another way. The chest compression sensor will work correctly in either orientation. Further, the instructions may be printed on the electrode in such a way that guides the user to the place and/or correct the orientation of the electrode without necessarily having to read the instructions closely. For example, the instructions may be intuitive and pictorial in nature, eliminating or reducing the use of words, so that the rescuer is able to internalize the guidance as quickly and as accurately as possible.

Further, a packaging for the electrode assembly can be configured in a way that makes it easy and efficient to access its contents, minimizing the amount of time a user will need to begin using the defibrillator.

Figure 1A:
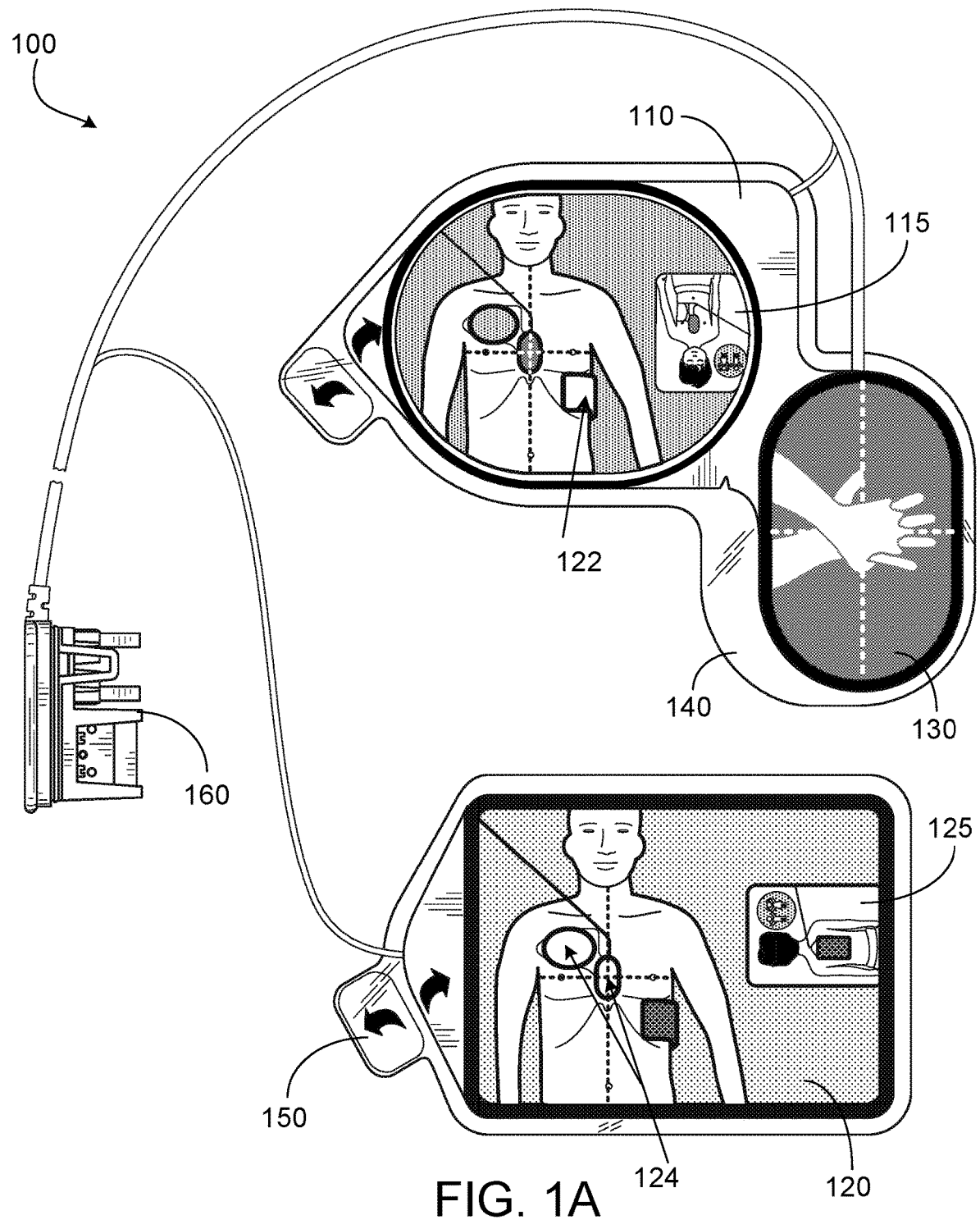
FIG. 1A shows an example of an electrode assembly.

FIG. 1A shows an example of an electrode assembly 100 capable of being used by different types of patients (e.g., adult patients and pediatric patients). The electrode assembly 100 includes a first electrode 110 which can be affixed to either an adult patient or a pediatric patient. The first electrode 110 may be attached to a chest compression sensor 130 in a way that enables the combination of the electrode and chest compression sensor 130 to be used in multiple orientations. For example, the electrode assembly 100 can be affixed to an adult patient in one orientation, and affixed to a pediatric patient in another orientation. Each electrode assembly contains three main elements: 1) an electrical connector for electrically connecting the electrode from the patient to the defibrillator discharge circuit; 2) conductive wires for connecting the electrical connector to the electrode; and 3) the electrode, which is composed of 3 elements: 3a) a conductive adhesive for connecting both electrically and adhering the electrode to the patient; 3b) a conductor for distributing the therapeutic current; and 3c) an insulating dielectric polymer film that covers the conductor from contact by the caregiver or other bystanders at the scene of the resuscitation.

The electrode assembly should be as flexible and conforming to the patient's body-shape, as possible. In general, a patient's torso is a complex geometric surface due to e.g. spine, sternum, breasts and armpits; these regions of complex geometry on the patient's thorax have non-zero Gaussian curvature. In differential geometry, the Gaussian curvature or Gauss curvature K of a surface at a point is the product of the principal curvatures, $\kappa_1$ and $\kappa_2$, at the given point:

$$K = \kappa_1 \kappa_2.$$

Figure 1B:
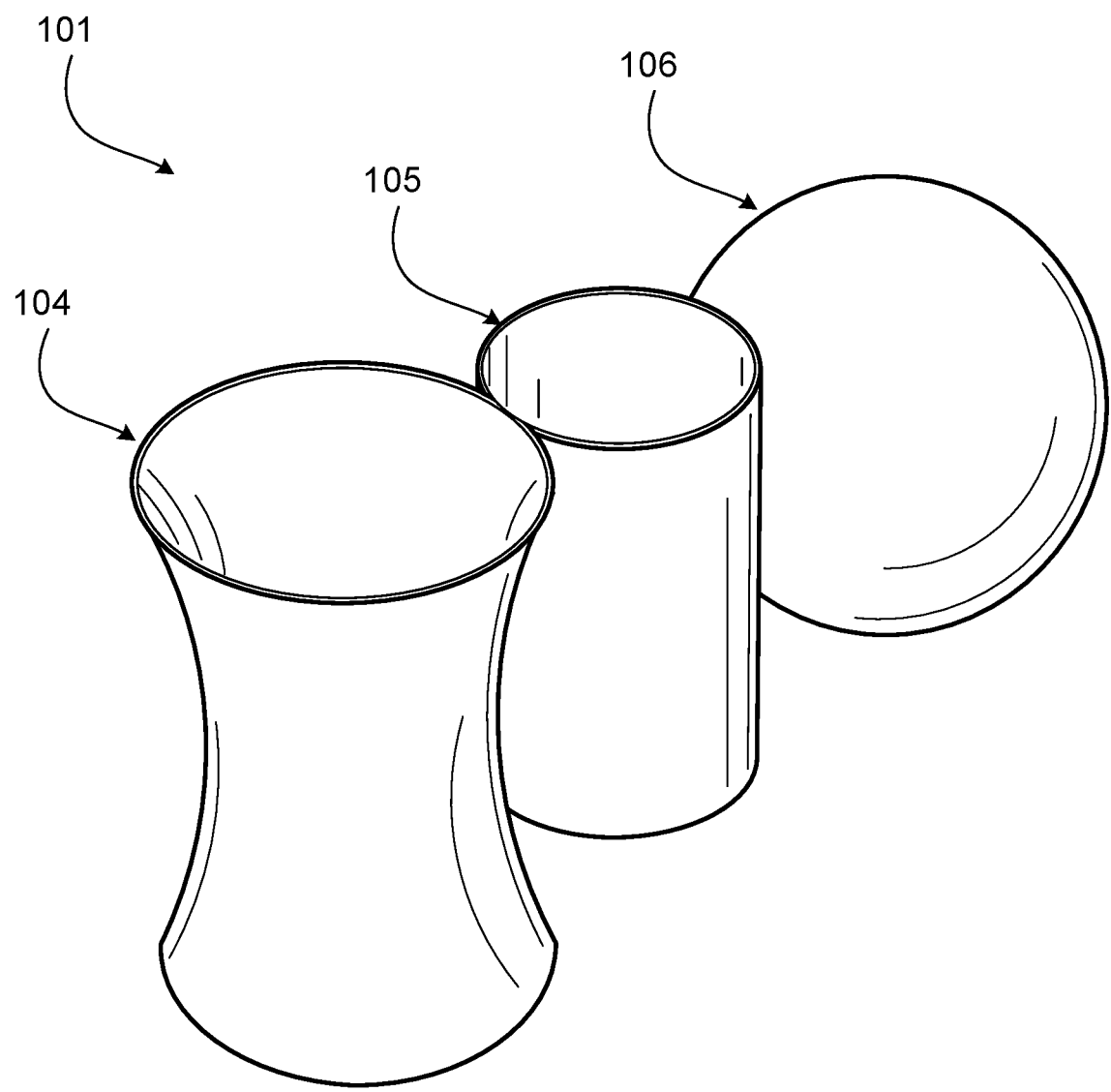
FIG. 1B shows examples of Gaussian surfaces.

For example, a sphere of radius r has Gaussian curvature $1/r^2$ everywhere, and a flat plane and a cylinder have Gaussian curvature 0 everywhere. The Gaussian curvature can also be negative, as in the case of a hyperboloid or the inside of a torus. Gaussian curvature is an intrinsic measure of curvature, depending only on distances that are measured on the surface, not on the way it is isometrically embedded in any space. From left to right in FIG. 1B shown below: a surface of negative Gaussian curvature 104 (e.g. hyperboloid), a surface of zero Gaussian curvature 105 (e.g. cylinder), and a surface of positive Gaussian curvature 106 (e.g. sphere). A surface with non-zero Gaussian curvature is also sometimes termed a "developable surface": that is, it is a surface that can be flattened onto a plane without distortion (i.e. "stretching" or "compressing"). Conversely, it is a surface which can be made by transforming a plane (i.e. "folding," "bending," "rolling," "cutting" and/or "gluing").

Conventional defibrillation electrodes currently have separate layers in the laminate structure for the dielectric function and laminated label that provides the printed instructions for use. As a result of this multiple laminate structure with printed top label, it is difficult for conventional conductive defibrillation electrodes to properly conform during the various manipulations of the patient during resuscitation, such as chest compressions. In accordance with embodiments of the present disclosure, the laminate structure of the electrode is collapsed into, at most, three layers with the dielectric layer also providing the printed label function: 3a) a conductive adhesive for connecting both electrically and adhering the electrode to the patient; 3b) a conductor for distributing the therapeutic current; and 3c) an insulating dielectric polymer film that covers the conductor from contact by the caregiver or other bystanders at the scene of the resuscitation, and also provides the printed instructions for use. Hence, since instructions for use are directly printed on to the dielectric layer, there is no need for the electrode to include a printed top label.

In some versions of the electrode, the electrode can be made more conformable by making the dielectric polymer film out of a stretchable material such as silicone or other polymer such as polyurethane. Further the conductor for distributing the electrical current may be made from conductive, polymer-based inks, such as the silver/silver chloride inks AGCL-675 or AGCL-823 manufactured by Conductive Compounds (New Hampshire). The conductive inks are typically thinner and less stiff than alternative metal foil conductors used in conventional defibrillation electrodes.

The pediatric patient can be a person (e.g. a child) who requires specialized or otherwise different treatment by the rescuer when using the electrode assembly or an automated external defibrillator (AED) In some embodiments, the pediatric patient may require treatment of a comparatively lower intensity than the adult patient, such as reduced energy levels of shock therapy, softer chest compressions, or the like. The pediatric patient can be physically smaller than the adult patient and, hence, it may be more suitable that the electrodes of the electrode assembly 100 be affixed at different places on the pediatric patient's body as compared to an adult configuration used by adult patients. For example, when using the adult configuration, it may be appropriate for the rescuer to affix one electrode to a patient's chest and another electrode to an intercostal region of the patient located opposite to the heart such that electric current flows through the heart of the patient during delivery of the electric shock therapy. Such placement is described in more detail with respect to FIG. 9. In another example, the pediatric patient's body can be sized such that it is more appropriate for a different orientation of the electrodes in the electrode assembly to be used than the adult configuration. For example, the electrodes of the electrode assembly might not fit on a pediatric patient if placed using the adult configuration. The one or more configurations can be used to ensure that the electrodes are placed on the patient at an appropriate distance apart such that, when shock therapy is applied, current can go through the heart of the patient.

As provided herein, the rescuer can be any person who is using the electrode assembly, assisting a user of the electrode assembly, or otherwise caring for the patient or assisting in the care of the patient.

In use, a rescuer may desire to quickly determine which configuration of the electrode assembly is appropriate depending on the type of patient. The components of the electrode assembly are manufactured using processes and materials that enable enhancements to their usability when deployed in a rescue situation. Some examples of these processes and materials are described briefly here and will be described greater detail below.

The upper (e.g., top) surface of the first electrode and/or chest compression sensor 130 may include a dielectric material (e.g., polypropylene, biaxially oriented polypropylene). The dielectric material may be formed on or otherwise cover other portions of the electrode and chest compression sensor. Alternatively, the dielectric material may be provided as at least a portion of a housing or other support for the electrode and/or chest compression sensor. The dielectric is of a type which can have clear, detailed, colorful images printed over the entire surface. These images can serve as instructions for using the electrode assembly that are easy to read and understand quickly by a rescuer, which can be useful in emergency situations. The material provided on the upper surface of the dielectric of the electrode may further allow for the printing of detailed, high resolution images directly thereon, without having to affix a separate label on to the electrode. By printing instructional images directly on to the dielectric material of the electrode, any additional labeling material, which has been conventionally laminated to the top surface of the electrode, can be eliminated. This helps to maintain the flexibility of the electrode, without interference from the additional labeling material, which may otherwise stiffen or mechanically hinder the overall electrode assembly in an undesirable manner.

The dielectric material may be able to withstand substantial voltages, such as those typically generated by the defibrillator (e.g., at least 800 V), without sustaining damage. This allows the electrodes to be used repeatedly and without concern that the therapeutic shock will be rendered ineffective, or will cause harm to the patient and/or rescuer. In various embodiments, the dielectric material is selected so as to be able to pass the IEC 601-2-25 "Working Voltage (dielectric strength)" test.

In various embodiments, the first electrode 110 and chest compression sensor 130 may be coated or otherwise provided an adhering substance (e.g. using one or more adhesive, conductive hydrogel, etc.) substances on a bottom surface or other surface intended to be adhered to the patient. In some examples, the chest compression sensor 130 is coated using a pressure-sensitive adhesive. In some examples, the electrode 110 is coated using a conductive hydrogel. The bottom surface of the first electrode includes an electrode contact. The contact may be used to apply an electric shock therapy during treatment and/or monitor one or more physiological parameters. The adhering substance may help one or more adhesive substances help to ensure that the contact can be firmly affixed to the patient during treatment and that the electric shock therapy is delivered to the patient. For example, as noted above, the substance can be a conductive hydrogel. The electrode contact can be behind the hydrogel layer. The hydrogel can couple the electrode 110 to the patient skin and provide a pathway between the patient and the electrodes. The bottom surface can be affixed to a backing 140 when the first electrode 110 and chest compression sensor 130 are not in use. In various embodiments, the first electrode 110 is sandwiched on either side by the polypropylene and backing 140.

In order to achieve an insulating dielectric polymer film layer that adequately performs the dual functions of protecting the rescuers from potentially lethal defibrillation voltages and also providing printed instructions for use on the electrodes themselves, the polymer film should have a dielectric that withstands an excess of 500-2500 volts. In addition, the surface of the dielectric polymer film should be capable of accepting printing with sufficient resolution to be able to accurately depict relevant patient anatomy and other instructional text and diagrams for placement and use of the electrodes during resuscitation. Poor wetting and adhesion in bonding, coating and printing processes that lead to reduced resolution are attributable to the low surface tension (SFT) of polymers, which is also referred to as the surface free energy (SFE). The low SFE is particularly unfavorable for the contact with aqueous adhesive and coating materials, which, owing to their high surface tension, are incompatible with polymers and tend to form droplets instead of wetting the surface.

Generally, adhesion is dictated by mutual polar and nonpolar (disperse) interactions between the polymer and the coating material. The greater the similarity between the solid material and the liquid coating in terms of their polar and disperse components, the better wetting will be and, as such, the stronger the adhesion. Many coating materials are based on the highly polar liquid water, making them generally unsuitable for interacting with predominantly disperse polymer surfaces. Pretreatment and cleaning increase wettability; improving wetting and adhesion on polymer surfaces means having to increase the SFE and its polar interactive component. This is accomplished through the application of high levels of electrical or thermal energy, as is done in corona, plasma, and flame methods, or through the use of reactive gases such as ozone. These treatment methods are based on oxidation processes, which introduce polar groups into the chemically nonpolar surface structure.

Figure 1C:
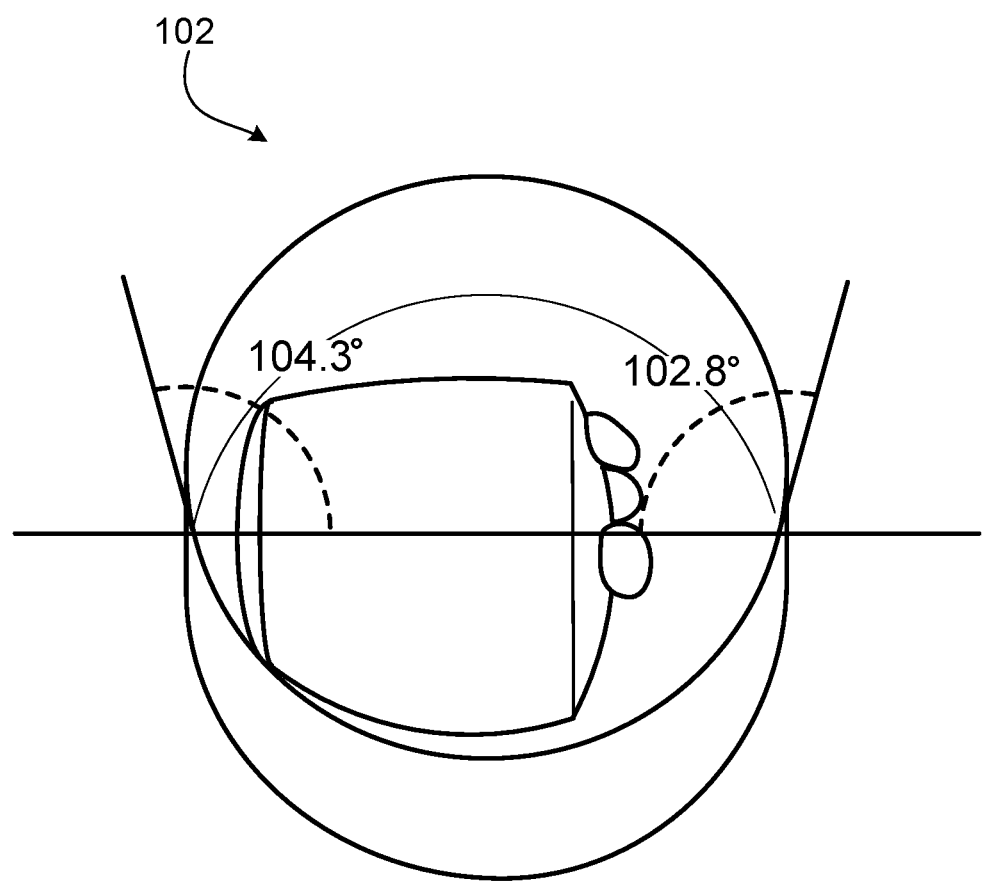
FIGS. 1C-1D show examples of contact angle measurements.
Figure 1D:
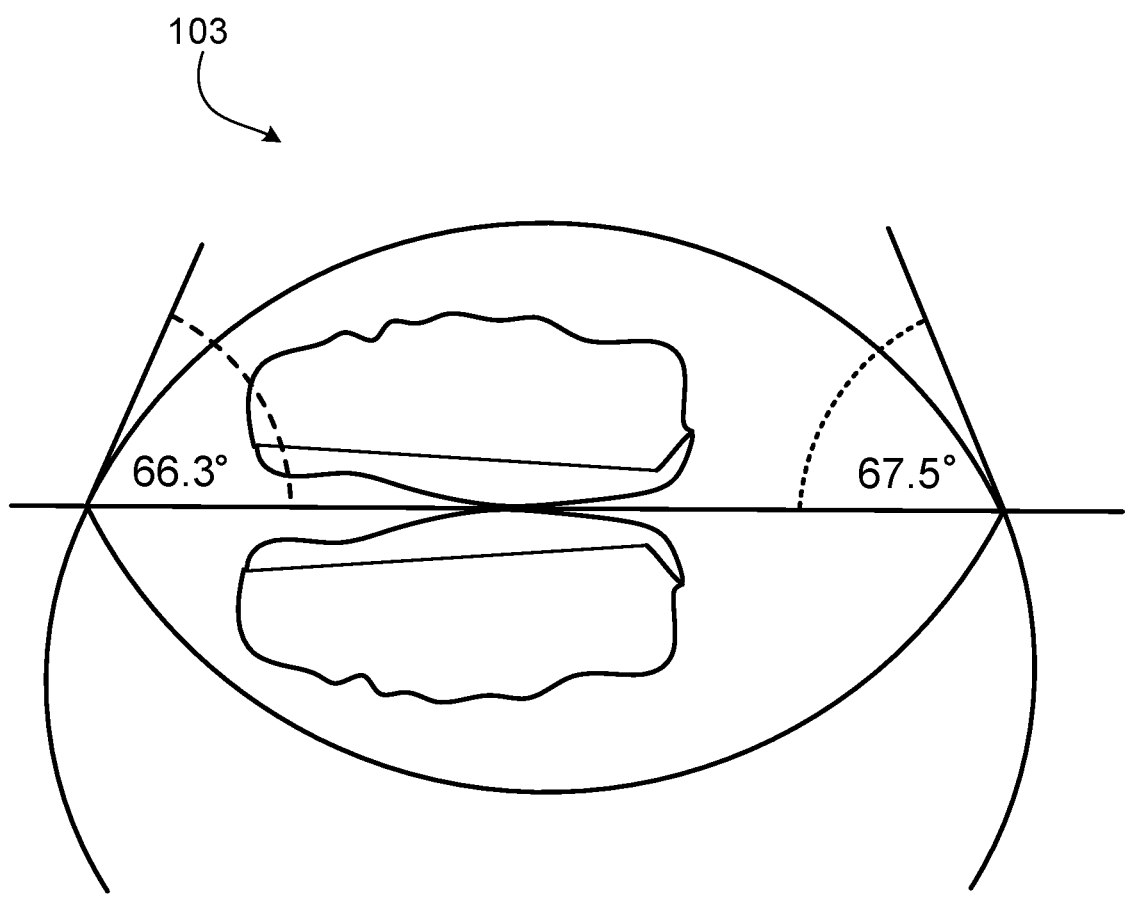

DIN 55660 recommends the contact angle method for determining the SFE of a solid. The contact angle, which reflects improvements to wettability achieved through pretreatment, describes the shape of a drop on the surface: the better the wetting, the flatter the drop will be, resulting in a smaller contact angle. Young's equation holds that the contact angle is a function of the SFE of the solid, the surface tension of the liquid, and the interfacial tension between the two phases. In order to determine the SFE and its polar and disperse components, contact angles are measured using multiple liquids for which the interactive components of the surface tension are known. Water, which is highly polar, and diiodomethane, which is a purely dispersed liquid, are two frequently used test substances. Not only do contact angle measurements yield information on the overall surface, they also detect differences in wettability across a single sample. Thus, position-dependent measurements (mapping) reveal whether the surface has been cleaned, activated or coated uniformly. There are a number of analytical methods that characterize the surface of plastics, and, in so doing, provide important information for optimizing coatings and adhesives (e.g.): 1) Taking optical measurements of the contact angle (drop shape analysis), static and dynamic; 2) Taking mechanical measurements of the contact angle using a tensiometer; 3) Determining surface free energy and its polar and disperse components; 4) Measuring surface tension of liquids; 5) Calculating adhesion and interfacial tension; 6) Measuring the roll-off angle of drops on hydrophobic surfaces. FIG. 1C shows an example of a contact angle measurement prior to surface treatment of a polypropylene material. FIG. 1D, shows the contrasting contact angle measurement after surface treatment of the material by plasma treatment.

In order to improve SFE of the polypropylene, or other plastic, film surface, a variety of surface treatments may be utilized. The main reason for poor adhesion with polyethylene is that the material is chemically inert and the carbonhydrogen bonding of the polyethylene molecules offers no linkages for the physic-chemical adhesion of ink molecules.

One method is to modify the surface chemistry of the film on which printing is going to occur. For instance, oxidation of the surface by some means, and the breaking down of the non-polar carbon-hydrogen bonds to form amine or carbonyl groups. This process would give rise to more polar (and therefore more wettable) surfaces. Such surface treatment methods may be methods, known to those skilled in the art, such as ultraviolet light treatment, corona discharge, plasma discharge or other electrical methods of treatment, solvent or other chemical treatment, flame or hot gas treatment, ozone treatment or other forms of surface activation. Accordingly, the surface treatment of the dielectric film may make the surface more suitable for printing thereon, while the dielectric still retains the ability to withstand high voltages typical of defibrillation.

Additionally, for some embodiments, the dielectric polymer film may be a lamination or co-extrusion of two or more polymers such that the underlayer or underlayers may have better dielectric or mechanical properties while the surface layer may have better printing properties. The co-extrusion or laminated structure may have two or more of the following, in addition to the top print layer: a "tie" layer that binds the multiple layers together; one or more "core" layers that may be optical enhancing layers for opacity or reflectance, or mechanical strengthening layers i.e. tear-resistance; a "barrier" layer to improve gas or vapor-permeation rates; an "adhesive" layer to bind to the conductive defibrillation electrode element.

In some embodiments, during the container's manufacturing process, the label is placed into the open mold, and when plastic resin is extruded into the mold, it conforms to the shape of the object. As a result, a flexible, defibrillation electrode that readily conforms to the complex multi-surface geometry of the patient's thorax can be attained that does not require additional labeling steps or equipment, and has a "no-label" appearance. Lamination materials may include PET, foil, OPP, PE, High-Density Polyethylene (HDPE), metallocene PE, Linear Low Density Polyethylene (LLDPE), CPP and metalized films.

The dielectric polymer film chemistry, surface treatment and an ink formulation are adjusted to achieve a high resolution printed image on the surface of the dielectric film, such that a sufficient level of detail is achieved in order to have sufficiently detailed written and graphical instructions, such as anatomical details showing defibrillation electrode placement, etc. In some embodiments, the print resolution exceeds 50 Dots Per Inch (DPI); in other embodiments, the DPI may exceed 72 DPI, 150 DPI, 200 DPI or 300 DPI, and as high as 1500 DPI. The printing may be monochrome or color. The standards used to measure DPI are known to those skilled in the art, as, for instance, IEC TS 29112. DPI is typically proportional to SFE and inversely proportional to contact angle. In some versions, the dielectric polymer film chemistry, surface treatment and the ink formulation are adjusted to achieve a contact angle of less than 80 degrees, or a range of 5-85 degrees.

The electrode assembly 100 may include a second electrode 120. In some examples, the second electrode can similarly include polypropylene on an upper surface and adhering substance on a bottom surface. The bottom surface of the second electrode includes an electrode contact. The bottom surface of the second electrode 120 can similarly be affixed to a backing 140 when the second electrode is not in use. The first electrode, 110 second electrode 120, and chest compression sensor 130 may be in electrical communication via an electrical cable and a connector 160. The connector 160 can interface with an automated external defibrillator.

For certain embodiments, and as shown in FIG. 1, the cable may extend laterally from the connector such that, when connected to the defibrillator, monitor and/or other appropriate medical device, the cable extends substantially parallel to the surface of the device. For example, rather than extending in a substantially perpendicular direction that protrudes out from the device, the cable may be less likely to snag or otherwise interfere with movement of the rescuer around the device. In some cases, when the connector is plugged in, the cable may wrap over the edge of the defibrillator, conveniently out of the way. As described above, the first electrode 110 and the second electrode 120 may be constructed using similar layers, although for some embodiments the construction of the electrodes may differ. The electrodes 110, 120 may each have an upper surface on which instructions for use are printed. The electrodes 110, 120 may each have a bottom surface which can be coated using an adhering substance (e.g. conductive hydrogel). Prior to use, the adhering substance intended to help affix the electrodes 110, 120 to a patient can be pre-attached to the backing 140. The bottom surface of each electrode has a conductive (e.g. metal) contact. The conductive contact can be used to apply an electric shock to the patient during treatment and/or monitor one or more physiological parameters. The adhering substance may ensure that each piece of the electrode is coupled to the skin of the patient during treatment so that treatment of the patient can be properly administered.

As described in more detail below with respect to FIGS. 9-10, in use, the first electrode 110 and the second electrode 120 can be placed on a patient in different locations for treatment depending on whether the patient is a pediatric patient or an adult patient. In one example, the first electrode 110 may be placed on an upper right side of the chest of the adult patient during treatment. In another example, the first electrode 110 may be placed on a lower left side of an intercostal region of the pediatric patient during treatment. Additionally, the second electrode 120 may be placed on the lower left side of the intercostal region of the adult patient during treatment. In another example, the second electrode 120 may be placed on a central region of the back of the pediatric patient during treatment.

The chest compression sensor 130 may contain a mechanism for detecting chest compressions and assisting the rescuer in performing chest compressions. In some examples, the chest compression sensor 130 can provide information for determining the depth of chest compressions being performed during treatment. In some examples, the chest compression sensor 130 can provide information for determining a number of factors relevant to CPR performance, such as the depth, rate and release of chest compressions being performed during treatment. The chest compression sensor 130 can have an accelerometer. The chest compression sensor 130 can have a foam housing for containing the accelerometer or other measurement device. The chest compression sensor 130 has an upper surface which can include the polypropylene material. The upper surface can display instructions for using the chest compression sensor 130. The chest compression sensor 130 also has a lower surface that may be adhered to the patient. The bottom surface may be coated with a substance suitable for adhering the sensor to the patient (e.g. a pressure-sensitive adhesive). The adhering substance can be used to help affix or otherwise couple the chest compression sensor 130 to the patient during treatment or the backing 140 when not in use.

As described in more detail below with respect to FIGS. 9-10, during treatment, the chest compression sensor 130 is placed on the center of the chest of the patient. The chest compression sensor 130 can be placed on the chest of the adult patient or the chest of the pediatric patient. The rescuer can place his hands over the sensor and compress the chest of the patient. When the chest of the patient is compressed, the chest compression sensor 130 can measure characteristics of the compression. For example, the chest compression sensor 130 can provide information for determining one or more of the rate of compressions, the depth of compression, the total time that compressions have been performed by the rescuer, the velocity of chest release, amongst other information.

The first electrode 110, second electrode 120, and chest compression sensor 130 can each be one or more of a different shape and/or size from the other pieces of the electrode assembly 100. The one or more of the different shape and size can assist the rescuer in distinguishing one piece of the electrode assembly 100 from the others when comparing the pieces of the electrode assembly 100 to the printed instructions. The one or more different shape and/or size can assist the rescuer in determining where the piece of the electrode assembly 100 should be placed on a patient. In some examples, the first electrode 110 is elliptical and the second electrode 120 is substantially rectangular (e.g., rectangular edges with rounded corners). Though, it can be appreciated that the first and second electrodes can have any suitable shape. In some examples, the chest compression sensor 130 can be smaller than the first electrode 110, the second electrode 120, or both. In other examples, the first electrode 110 can be smaller than the second electrode 120.

As described above, the first electrode 110 in the electrode assembly 100 can include the polypropylene material on an upper (e.g. the top) surface. The polypropylene material can be a dielectric material able to withstand significant voltages (e.g., for defibrillation) without damage. The polypropylene material can be a film designed for applications including printing, lamination, vacuforming, label dispensing, and other processes performed by industrial converter companies. The polypropylene material can be semi-conformable, or may otherwise have the ability to conform to other surfaces via mutual contact. For example, the polypropylene can be flexible such that the material conforms to a rigid or semi-rigid surface, and can be twisted, bent, or similarly manipulated. In some implementations, the polypropylene material can be of the type MACtac PJ4512 Vivid 2 White Polypropylene produced by MACtac of Stow, Ohio. In some implementations, the polypropylene material can be a 1-4 mm (e.g., 2.6 mm) topcoated white biaxially oriented polypropylene with an aggressive quick tack permanent adhesive. In some implementations the polypropylene material can be white and suitable for having color images printed directly onto the surface of the polypropylene material. In some implementations the polypropylene can be top-coated, pearlescent, or both. The polypropylene material can have a thickness of 0.001 to 0.01 inch, 0.001 to 0.005 inches, 0.001 to 0.004 inches, 0.002 inches to 0.003 inches, or any other suitable thickness. The polypropylene can have an approximate elongation strength percentage of between 5-20%, 10-15% (e.g., 12%), or other suitable percentage in the machine direction and an approximate elongation strength percentage of 30-60%, 40-50% (e.g., 45%), or other suitable percentage in the cross-machine direction. The polypropylene can have an approximate tensile strength of 5-30 pounds-per-inch, 10-20 pounds-per-inch (e.g., 14 pounds-per-inch), or other appropriate tensile strength in the machine direction and an approximate tensile strength of 50-100 pounds-per-inch, 70-90 pounds-per-inch (e.g., 80 pounds-per-inch), or other appropriate tensile strength in the cross-machine direction.

The characteristics of the polypropylene material may allow for detailed, colorful images to be printed onto the surface of the polypropylene material in high resolution. Detailed images can have complex figures, words, or other marks drawn using precise lines, dots, and the like. Detailed instructions using a plurality of colors can be printed onto the upper surface of the electrodes 110, 120.

In some embodiments, as noted above, the polypropylene material of one or more of the electrodes may include an adhering substance, such as a conductive hydrogel and/or a polypropylene adhesive, including a rubber-based adhesive. The polypropylene adhesive can be a PJ4512 Polyfilm adhesive produced by MACtac of Stow, Ohio. The adhesive may have any appropriate combination of characteristics. In some examples, the polypropylene adhesive can be 705 VHP high-tack permanent adhesive. The polypropylene adhesive can have a thickness of approximately 0.001 to 0.003 inches, approximately 0.001 inch to 0.002 inches, approximately 0.0012 inches to 0.0016 inches, approximately 0.00136 inches to 0.00154 inches, or a thickness falling with any other suitable range. The 180° peel adhesion can be approximately 3-5 pounds-per-inch (e.g., approximately 3.7 pounds-per-inch) for high-density polyethylene, and approximately 4-7 pounds-per-inch (e.g., approximately 5.4 pounds-per-inch), or any other suitable adhesion strength for stainless steel. The one-inch loop tack can be approximately 1-5 pounds-per-inch (e.g., approximately 3.5 pounds-per-inch) for high-density polyethylene and approximately 0.1-3.0 pounds-per-inch (e.g., 0.9 pounds-per-inch) for wood, for example. The polypropylene adhesive can be applied in temperatures including and greater than 20° Fahrenheit. The polypropylene adhesive can perform nominally at temperature ranges of approximately −65° Fahrenheit to 160° Fahrenheit.

In some implementations, materials that are used for the electrode assembly can be radiolucent such that the electrode assembly minimizes interference with x-ray radiation used for imaging the chest of the patient. The electrode assembly can be configured so that x-ray images taken of the patient are not blocked or disrupted by the electrode assembly and a clear x-ray image of the patient's chest, including the areas under the electrodes, can be seen. Such materials can include the polypropylene material, the polypropylene adhesive, the pressure sensitive adhesive, the ink formulation (e.g., conductive polymer based inks such as silver/silver chloride), metallic electrodes, hydrogel, and other materials of the electrode assembly.

In some examples, the second electrode 120, the chest compression sensor 130, or both can similarly include the polypropylene material. The polypropylene can be similarly affixed to the second electrode 120, chest compression sensor 130, or both using an adhering substance, such as a conductive hydrogel and/or a polypropylene adhesive.

The polypropylene material which is included in or on one or more of the first electrode 110, the second electrode 120, and the chest compression sensor 130 may have instructions which are printed on the upper surface visible to a rescuer using the electrode assembly 100. The instructions can be printed onto the polypropylene material. The polypropylene material on the first electrode 110 has instructions printed on the upper surface. In some examples, the instructions cover substantially all of the upper surface of the first electrode 110. Substantially all of the upper surface can be the entire surface. By "substantially all" it is meant that the instructions can cover the entire upper surface, or all of the upper surface except for a small portion such as a small border near the edge of the surface. Substantially all of the upper surface is generally at least 80% of the upper surface and typically up to 99% or more of the surface. In some examples, the pictorial instructions cover a majority of the upper surface. The majority of the upper surface can be a portion of the upper surface greater than 50%. The coverage described here is typically greater than coverage by a sticker or label affixed to the upper surface which covers a portion of the surface. When a majority or substantially all of the surface includes the instructions, the larger surface area of the instructions allows for larger, more detailed instructions to be printed on the upper surface. In turn, the instructions can be more clearly identified and interpreted by a rescuer, which can greatly assist the rescuer during treatment. In some examples, the instructions are a pictorial representation of the placement of the first electrode 110 on a patient. Pictorial instructions can include non-textual representations (e.g. pictures) of how to use the electrode assembly 100. The pictorial instructions can provide the rescuer with a clear and concise description of how to use the electrode assembly 100. The pictorial instructions can be understood by the rescuer quickly, facilitating treatment. The instructions can have many colors. In one example, the instructions can have seven or more colors. The colors can assist the rescuer in determining where the first electrode should be placed on a patient during treatment. The second electrode 120 and the chest compression sensor 130 can also be similarly covered by instructions.

As described above and as shown by FIGS. 2-3, the instructions on the upper surface of the first electrode 110, the second electrode 120, and the chest compression sensor 130 can include one or more of a background, instructions for adult use, instructions for pediatric use 115, 125, and instructions for removing the backing 150. In one example, the background of the instructions can be a distinctive color. The background can cover a substantial portion of the electrode 110, 120. In various embodiments, the substantial portion can be greater than 30%, greater than 40%, or greater than 50% of the upper, exposed surface of the electrode. The substantial portion can be enough of the upper surface that it covers more of the surface than any other color. For example, the distinctive color can cover enough of the upper surface of the first electrode 110 so that the rescuer is more likely to associate the color with the first electrode 110. The distinctive color of the first electrode 110 can be different than the distinctive color(s) of the second electrode 120 and the chest compression sensor 130. The association of a color with each electrode 110, 120 and the chest compression sensor 130 can be useable to assist a rescuer with understanding the instructions instructing the rescuer where and how to place each electrode 110, 120 and the chest compression sensor 130. In some embodiments, the instructions for pediatric use 115, 125 can be further distinguished from the other instructions by a pediatric symbol placed proximately to the instructions for pediatric use 115, 125.

As described above and as shown by FIGS. 2-3, in some implementations, one or more of the instructions for adult use, the instructions for pediatric use 115, 125, and the instructions for removing the backing 150 are pictorial instructions. The pictorial instructions can illustrate where on the particular patient each piece of the electrode assembly 100 should be placed for treatment. The first electrode 110, the second electrode 120, and the chest compression sensor 130 can each be represented as a shaded or filled object in the instructions. The color of the shading or fill for the object can match or be approximately the same color as the background color (e.g. the backgrounds 220, 320 described with respect to FIGS. 2-3) of the piece of the electrode assembly represented by the object. For example, the color depicting the electrode shape on the diagrams themselves can be a simplified representation of the pictorial instructions, represented by the prominent background color on the image. As an example, if the piece of the electrode assembly has a green-yellow background, the piece can be represented as an object having a similar shape that is shaded or filled with an approximately corresponding green-yellow color in the instructions. The relative shapes and sizes of the objects in the instructions can substantially match the shapes, sizes, or both of the first electrode 110, second electrode 120, and chest compression sensor 130. In one example, the objects representing the pieces of the electrode assembly 100 other than the one on which the instructions are printed can be illustrated as faded so that the relevant object of interest is more visually prominent. For example, in the instructions on the first electrode 110, the object 122 representing the second electrode 120 can be faded or discolored to a degree such that the object(s) 124 representing the first electrode 110 and attached chest compression sensor 130 are more emphasized. In such cases, it may not be necessary for objects and backgrounds depicting the electrodes to be color-coded, as discussed above.

The instructions for using the electrodes 110, 120 and chest compression sensor 130 may be printed in a particular orientation on the upper surface of each electrode and the chest compression sensor 130. Each of the instructions can be oriented on the surface of each electrode so that the instructions are in a readable orientation when the electrode is in the correct orientation for placement on a particular patient for treatment. In some examples, on the first electrode 110 the instructions for pediatric use 115 are rotated approximately 180 degrees from the instructions for adult use. In other examples, on the second electrode 120 the instructions for pediatric use 125 are rotated approximately 90 degrees from the instructions for adult use. Though, it can be appreciated that the instructions for adult and pediatric use of the electrodes may be oriented in any other appropriate manner. In other implementations, the instructions for placing the chest compression sensor 130 include one or more patterns, such as a dashed cross, which (through alignment thereof) may assist the rescuer in placing the chest compression sensor 130 in the correct orientation and location on a particular patient. The pattern can also be provided on a representation of the particular patient in the instructions on the electrodes to assist the rescuer in placement of the chest compression sensor relative to the electrodes for the particular patient. In other examples, the chest compression sensor 130 can have pictorial instructions on the surface depicting hand placement, hand configuration, or both for using the chest compression sensor.

Figure 2:
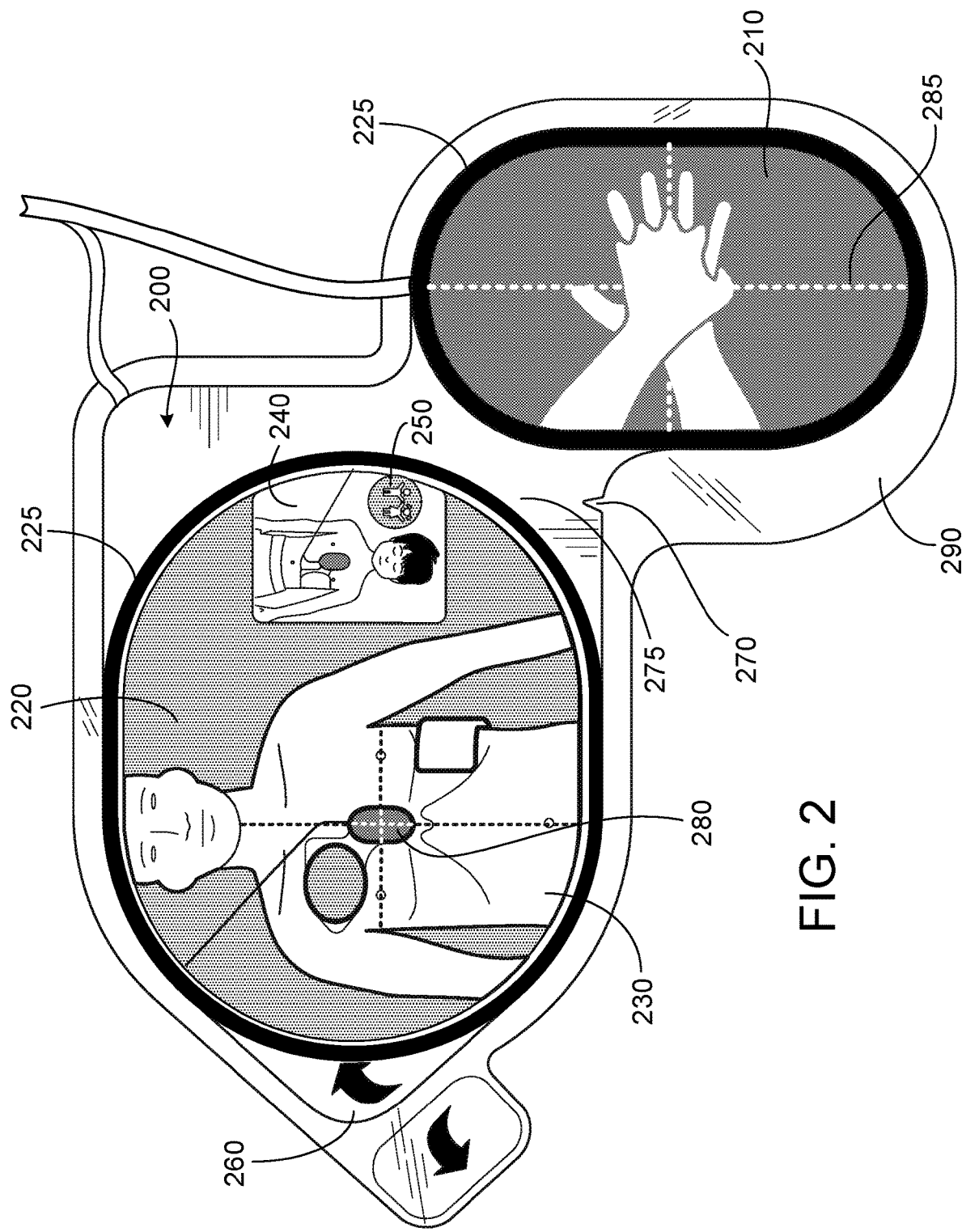
FIG. 2 shows an example of an electrode.

FIG. 2 shows an example of an electrode 200. This electrode could be an example of the first electrode 110 shown in FIG. 1. The electrode 200 is attached to a chest compression sensor 210 (e.g., the chest compression sensor 130 shown in FIG. 1). In some implementations, the electrode 200 and the chest compression sensor 210 are attached to one another by an extension 275 of the electrode. In some implementations, the electrode 200 and the chest compression sensor 210 are in a fixed orientation relative to one another. The fixed orientation can assist the rescuer in placing the electrode 200 and the chest compression sensor 210 in the correct relative positions on the patient during treatment. The chest compression sensor 210 can be detachable from the electrode 200. The extension 275 of the electrode 200 may have a notch 270 which facilitates the detachment of the chest compression sensor 210 from the electrode 200. In one example, the chest compression sensor 210 can be detached by tearing the extension 275 of the electrode 200 at the notch 270. As described above in reference to FIG. 1, the electrode 200 and chest compression sensor 210 each have an upper surface (e.g. a top surface) which can include a polypropylene material. In some implementations, pictorial instructions for using the electrode 200 and chest compression sensor 210 can be printed onto the polypropylene material. As described above in reference to FIG. 1, the electrode 200 and the chest compression sensor 210 each have a bottom surface which can be coated using a adhering substance (e.g. a conductive hydrogel, one or more adhesive material). substances. In some examples, the adhering chest compression sensor can have a bottom surface coated using a pressure-sensitive adhesive. In some examples, the electrode can have a bottom surface coated using a conductive hydrogel. In some examples, the adhesive substance is used to affix or substantially maintain the position of the electrode 200 and the chest compression sensor 210 against the patient during use. In some implementations, the electrode 200 and chest compression sensor 210 can be affixed to a backing 290 when not in use. In some implementations, the chest compression sensor 210 is reusable.

The chest compression sensor 210 can be attached to the electrode 200 for several reasons. Such attachment can encourage and facilitate proper use of the electrode assembly. For example, the number of components which the rescuer orients and places on the patient during use may be reduced. In another example, the chest compression sensor can assist the rescuer in placing the electrodes by providing a reference point, as described in further detail with respect to FIGS. 9-10. The rescuer can be more likely to use the chest compression sensor 210 and get valuable feedback data which can be used to assist the rescuer during the CPR process than for a chest compression sensor which is not attached to the electrode 200. The chest compression sensor can be easier to configure correctly relative to the electrodes by the rescuer.

Figure 3:
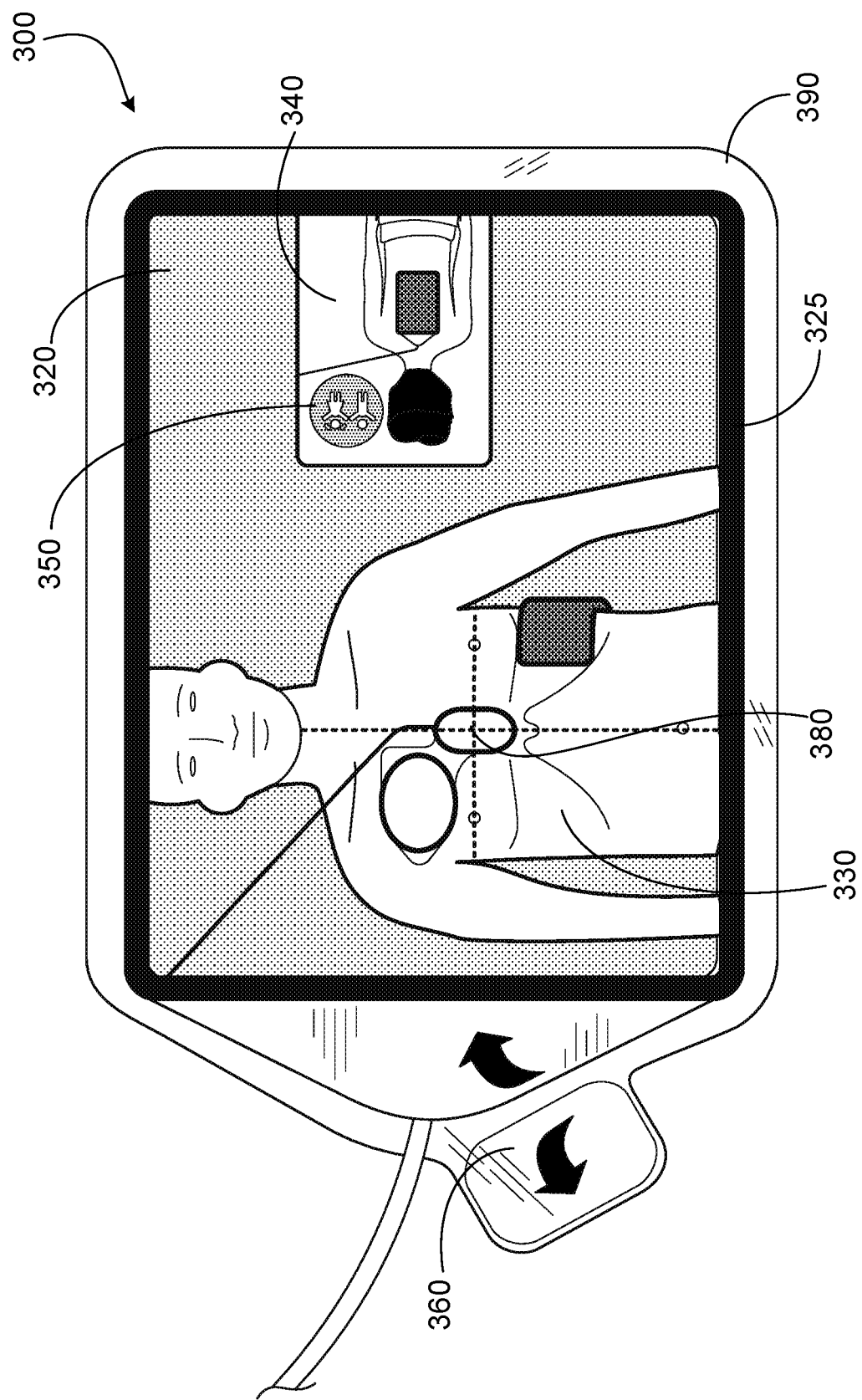
FIG. 3 shows an example of an electrode.

FIG. 3 shows an example of an electrode 300. This electrode could be an example of the second electrode 120 shown in FIG. 1. As described above in reference to FIG. 1, the electrode 300 has a upper surface which can include a polypropylene material. In some implementations, pictorial instructions for using the electrode 300 can be printed onto the polypropylene material. As described above in reference to FIG. 1, the electrode 300 has a bottom surface which can be coated using an adhering substance (e.g. a conductive hydrogel, adhesive). In some examples, the adhering substance is used to couple the electrode 300 to the patient during use. In some implementations, the electrode 300 can be affixed to a backing 370 when not in use.

The instructions for using the electrodes 200, 300 and the chest compression sensor 210 can include several features. The instructions can include a background 220, 320, a borderline 225, 325, adult use instructions 230, 330, pediatric instructions 240, 340, and indications 260, 360 for removing the backing 290, 390. The instructions which appear on each piece of the electrode assembly 100 are consistent for each electrode 200, 300 and the chest compression sensor 210 in the electrode assembly 100.

The instructions on each of the electrodes 200, 300 include a background 220, 320 which can cover a significant portion of the electrodes 200, 300. In some examples, the background 220, 320 of each electrode is a color which is noticeably different and readily distinguishable from colors used elsewhere in the instructions except where the color or an approximately similar color is used to represent the electrode on which the background color is printed, as described above with respect to FIG. 1. In some implementations, the background 220 color of the electrode 200 matches a chassis color of the automated external defibrillator with which the electrode 200 is associated. The matching background 220 can help the rescuer confirm whether the electrode 200, and consequently the electrode assembly 100, are associated with the particular automated external defibrillator. As described above with respect to FIG. 1, the background color is used to represent the electrode in the pictorial instructions for using the electrode 230, 240, 330, 340.

The background color 220, 320 may extend to a thick borderline 225, 325 which can extend around the perimeter of the electrodes 200, 300. The borderline 225, 325 can highlight the shape of the electrodes 200, 300. In some examples, the shape and size of the electrode 200 can be different than other pieces of the electrode assembly 100 so that the rescuer can more easily distinguish each electrode 200, 300 and the chest compression sensor 210 in the instructions. In one example, the electrode 200 is an oval shape. In other examples, the electrode 200 can be a circle, rectangle, parallelogram, or other appropriate shape. The shape of the electrode 200 can be asymmetrical. In another example, the electrode 200 is larger than the chest compression sensor 210, although for some embodiments, the electrode is not larger than the chest compression sensor. In other implementations, the electrode 300 is substantially rectangular and/or may include truncated edges (e.g., beveled, rounded, etc.). Similar to the electrode 200, the electrode 300 can be a circle, oval, rectangle, or other appropriate shape. The shape of the electrode 300 can be asymmetrical. In other implementations, the second electrode 300 can be larger than the first electrode 200, although it is not a required aspect of the present disclosure for the second electrode 300 to be larger than the first electrode 200.

In several implementations, the chest compression sensor 210 has a similar background and borderline, where the chest compression sensor background color is different from the electrode background 225. In some examples, the chest compression sensor 210 can have instructions for placement of the hand(s) or other chest compression device (e.g., automated compression device, active compression decompression device, amongst others) for use during CPR. The chest compression sensor 210 can be represented using instructions in a similar manner as the electrode 200. Other shapes than the shapes of each piece of the assembly can be used for the backing 140 of each respective piece.

In some examples, the colors of the backgrounds electrodes 220, 320 and the chest compression sensor are provided such that colorblind rescuers can distinguish the electrodes 200, 300 and chest compression sensor 210 from one another. In some examples, the colors are soothing, non-stressful colors such as green, yellow, purple, blue, or other colors that are less likely to induce alarm (e.g., bright red might be more likely to cause alarm than a comparatively softer color). In some implementations, the electrode background 220 can be green-yellow, the electrode background 320 can be blue, and the chest compression sensor background can be purple. For example, on a standard 0-255 Red Green Blue (RGB) scale, the green-yellow color can have RGB values of approximately Red 155 (e.g., between 150-160), Green 166 (e.g., between 160-170), and Blue 57

(e.g., between 50-65). The blue color can have RGB values of approximately Red 85 (e.g., between 80-90), Green 135 (e.g., between 130-140), and Blue 185 (e.g., between 180-190). The purple color can have RGB values of approximately Red 90 (e.g., between 80-100), Green 50 (e.g., between 40-60), and Blue 110 (e.g., between 100-120). Each RGB value can be within a range of 30 points higher or lower than the value stated above. Alternatively, other color combinations may be used. In general, the colors employed may be those that are dissimilar, and which may assist in providing the user with a clear understanding of how the electrodes should be placed.

Adult use instructions 230 are printed onto the upper surface of the electrodes 200, 300. The adult use instructions 230, 330 show an adult figure and the pieces of the electrode assembly 100 in the proper locations and orientations on the adult figure's body. For example, the electrodes 200, 300 can be represented by the background colors 220, 320 and shapes of each electrode 200, 300. Likewise, the chest compression sensor 210 can be represented by the chest compression sensor background and shape. A pattern can be used to instruct the rescuer as to the proper orientations of the electrodes 200, 300 and chest compression sensor 210. In the example shown in FIG. 2, a dashed cross 280 or other indicator may be printed on the adult. A similar dashed cross 285 or other indicator may be printed on the chest compression sensor 210 so that the rescuer can orient the chest compression sensor properly and place it in the approximately correct position on the patient. In some implementations, since the electrode 200 and the chest compression sensor 210 are attached, correctly orienting the chest compression sensor 210 will automatically correctly orient the first electrode 200. In some examples, the electrode 300 is represented as faded on the instructions 230 so that the rescuer can more easily distinguish and focus on the relevant instructions for the first electrode 200 and the chest compression sensor 210. In some examples, the electrode 200 and chest compression sensor 210 are represented as faded on the instructions 330 so that the rescuer can more easily distinguish and focus on the relevant instructions for the second electrode 300.

Pediatric instructions 240 are printed onto the upper surface of the electrodes 200, 300. In the examples shown in FIG. 2-3, the pediatric instructions are displayed using an inset in the backgrounds 220, 320 of the electrodes 200, 300. The inset can help distinguish the pediatric instructions 240, 340 from the adult instructions 230, 330 on each electrode 200, 300. The pediatric instructions 240, 340 can be further distinguished by locating the pediatric symbol 250, 350 inside of the inset. The pediatric instructions 240, 340 show a child and respective pieces of the electrode assembly 100 in the proper locations and orientations on the child's body. The pieces of the electrode assembly 100 are represented in a manner consistent with the adult instructions and across each piece of the electrode assembly 100. In some examples, the relative sizes, colors, and shapes of the electrode 200 and chest compression sensor 210 are approximately the same in the pediatric instructions as the adult instructions 230.

Indications 260, 360 for removing the backing 290, 390 are displayed on the upper surface of the electrodes 200, 300 and on the backing 290, 390. The indications 260, 360 show where a rescuer can peel away the electrode 200 from the backing 290. The indications 260, 360 can be represented by arrows. The indications 260, 360 are described in more detail relating to FIGS. 4-5.

The adult instructions 230, 330 and pediatric instructions 240, 340 are presented in orientations which aid the rescuer in reading and understanding the instructions when using the electrodes 200, 300 and chest compression sensor 210. The adult instructions 230, 330 are printed such that the orientation of the electrodes 200, 300 as pictured on the adult figure will match the perspective of the rescuer when treating the patient. Hence, when the electrodes 200, 300 are oriented in the preferred position on the adult patient, the pictures corresponding to the adult figure appear as right side up to the rescuer, whereas the pictures corresponding to the pediatric figure may be at a different orientation (e.g., angled, 90 degrees, 180 degrees, etc.). In one implementation, as shown in FIG. 2, the electrode 200 is oriented to the left of the chest compression sensor 210 from the perspective of the rescuer when treating an adult patient. The adult instructions 230 are printed such that they match the orientation of the adult patient when treating the adult patient. Similarly, the pediatric instructions 240 are printed such that they match the orientation of the pediatric patient when treating a pediatric patient. Accordingly, when the electrodes 200, 300 are oriented in the preferred position on the pediatric patient, the pictures appear as right side up to the rescuer, whereas the pictures corresponding to the adult figure may be at a different orientation (e.g., angled, 90 degrees, 180 degrees, etc.). In some examples, when treating the pediatric patient, the electrode 200 is rotated approximately 180 degrees relative to the orientation for an adult patient. In such examples, the pediatric instructions 240 are printed using an approximately 180 degrees rotation relative to the orientation of the adult instructions 230. The pattern on the chest compression sensor 285, such as a cross, can help the rescuer orient the first electrode 200 and chest compression sensor 210 for both pediatric and adult patients. It can be appreciated that the adult and pediatric specific instructions may be oriented in any suitable manner relative to one another.

The relative orientations of the instructions 330, 340 are of similar significance for the electrode 300. In one implementation, as shown in FIG. 3, the electrode 300 is oriented laterally on an intercostal region of the adult patient from the perspective of the rescuer when treating an adult patient. The adult instructions 330 are printed such that they match the orientation of the adult patient as viewed by the rescuer when treating the adult patient. Similarly, the pediatric instructions 340 are printed such that they match the orientation of the pediatric patient as viewed by the rescuer when treating a pediatric patient. In some examples, when treating the pediatric patient, the electrode 300 is rotated approximately 90 degrees relative to the orientation for an adult patient. In such examples, the pediatric instructions 340 are printed using an approximately 90 degrees rotation relative to the orientation of the adult instructions 330, although other orientations may be possible. The descriptions of FIGS. 9-10 below provide more detailed descriptions of using the electrodes 200, 300 and chest compression sensor 210 for adult and pediatric patients.

Figure 4:
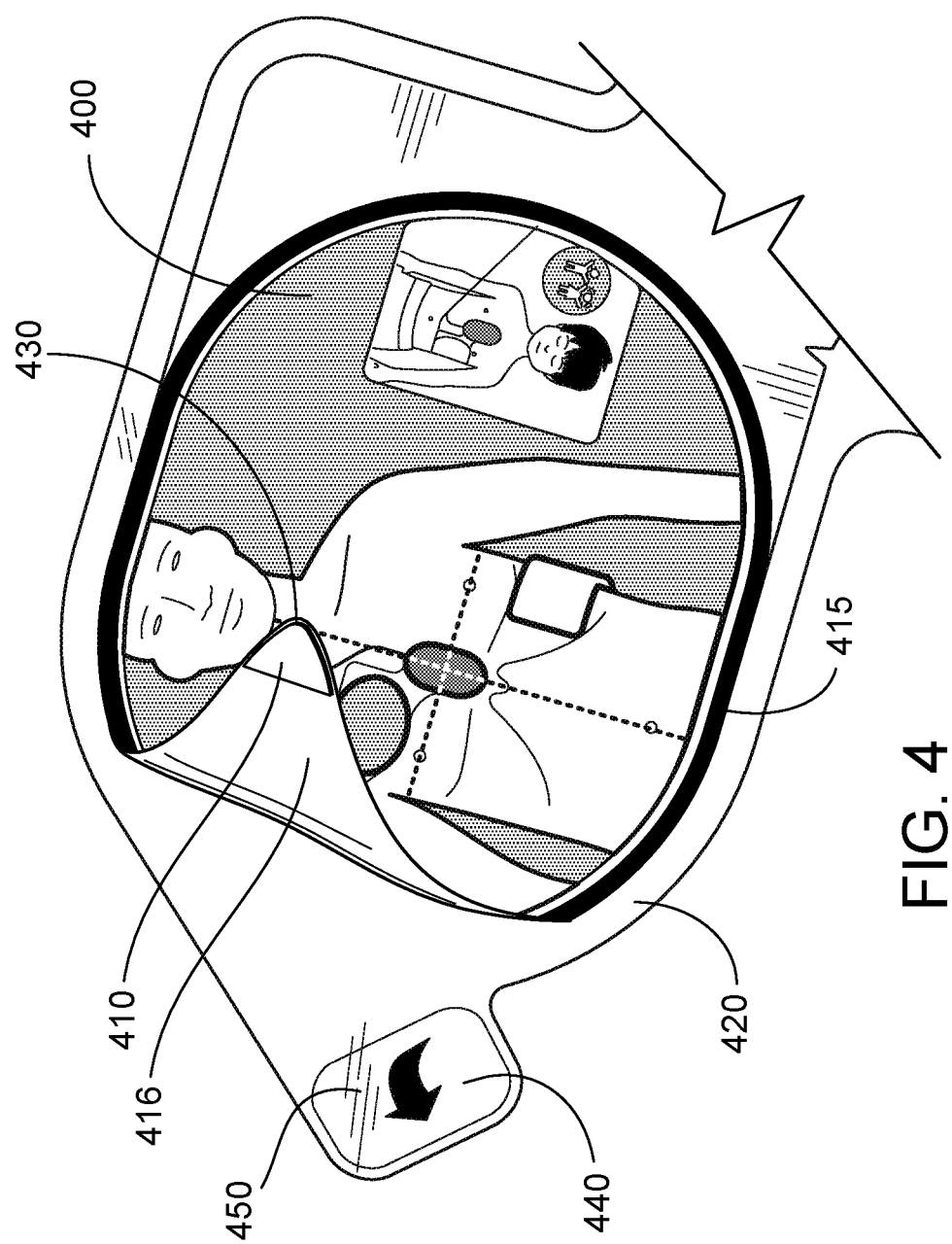
FIG. 4 shows an example of an electrode being removed from the backing.
Figure 5:
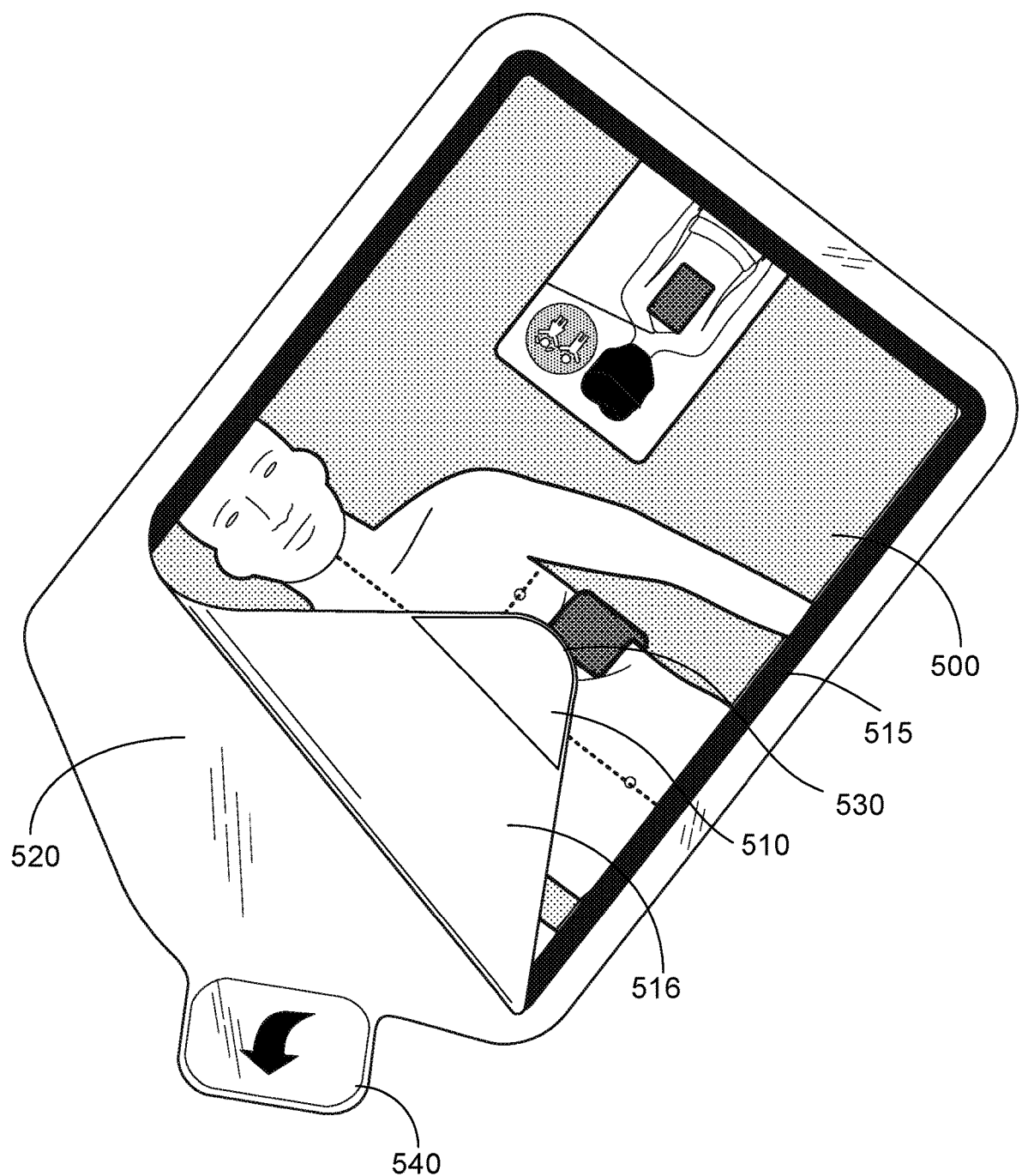
FIG. 5 shows an example of an electrode being removed from the backing.

FIGS. 4 and 5 show examples of the layers on the electrodes 110, 120. In FIGS. 4-5, an electrode 400, 500 is shown which has an upper (e.g. a top) surface 415, 515, a bottom surface 416, 516, a backing 420, 520, and a pull tab 430, 530. The backing 420, 520 also has a pull tab 440, 540. The pull tab 430, 530 shares the upper surface with the body of the electrode 400, 500. The bottom surface 416, 516 of the electrode 400, 500 is coated using an adhesive substance (e.g. a conductive hydrogel as an adhering substance) as described in relation to FIG. 1A above, and the adhering substance can serve to maintain coupling between the electrode 400, 500 and the respective backing 420, 520 when the electrode is not in use. The pull tab 430, 530 has a bottom tab surface 410, 510 which is not coated with adhering substance and so does not stick to the backing 420, 520. For certain embodiments, it may be preferable for at least a portion of the pull tabs (used for removing the electrode from the backing) to be void of adhesive so as to allow responders (e.g., wearing gloves) to easily apply the electrodes without having sticky portions adhere to their fingers in an undesirable manner.

In some implementations, the pull tab 430, 530 is an extension of the electrode 400, 500. The pull tab 430, 530 can be a tapered edge or extension of the electrode 400, 500. In some examples, the pull tab 430, 530 can have the same upper surface as the electrode 400, 500. For example, the polypropylene material that can be included with the electrode 400, 500 can also be included with the pull tab 430, 530. An upper surface of the pull tab 430 can have an indicator 450 which indicates to the rescuer where to grasp the electrode 400, 500 when removing the electrode 400, 500 from the backing 420, 520 and applying it to the patient. The indicator 450 can be a symbol and/or may include an illustration showing the user how to handle the electrode(s). For example, in FIGS. 4-5, the indicator is an arrow. Or, for some embodiments now shown, the indicator may include an illustration of a finger, arrows or other intuitive depiction for instructing the user. As shown in FIGS. 4-5, the backing 420, 520 also has a similar indicator which matches the indicator 450. The bottom tab surface 410, 510 can be a non-stick surface which can be gripped by a rescuer when handling the electrode 400, 500 and removing it from the backing 420, 520.

Figure 6:
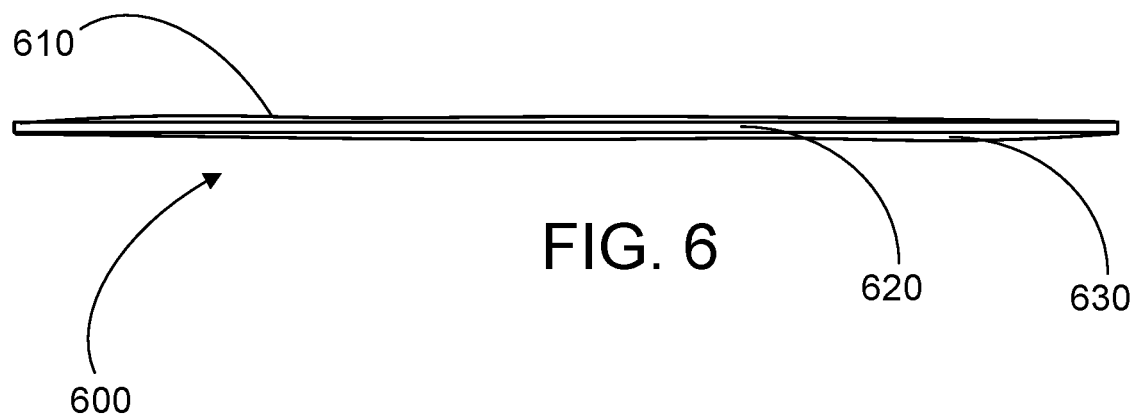
FIG. 6 shows an example of a profile of an electrode.
Figure 7:
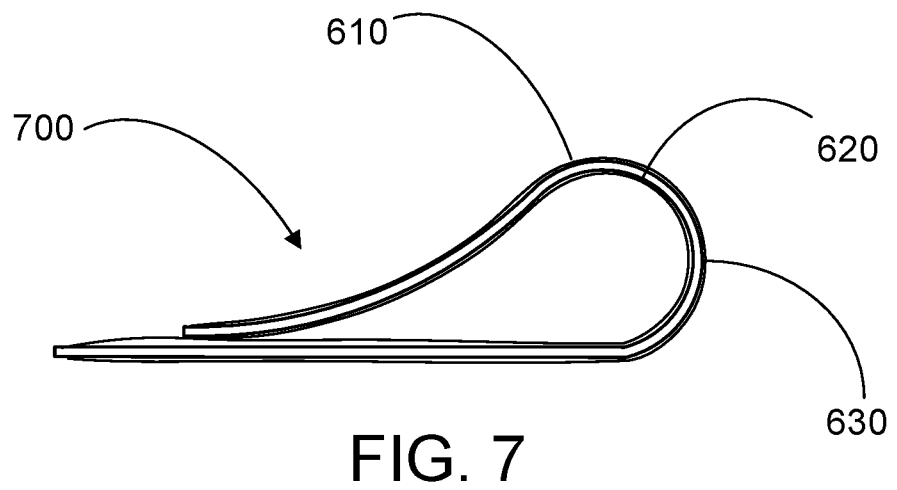
FIG. 7 shows an example of a profile of an electrode being bent.

FIGS. 6 and 7 show examples of properties of an electrode 600, which can be, for example, the first electrode 110 or the second electrode 210 in the electrode assembly 100. FIG. 6 shows dimensions of an example electrode from a profile view. An upper surface 610, a bottom surface, 620, and a backing 630 are visible and form sandwiched layers. The upper surface (e.g. a top surface) can include the polypropylene material. The polypropylene can be sandwiched between upper surfaces. In some examples, the sandwiched layers of the electrode are substantially thin. For example, the thickness of the electrode can be between 0.1-5 mm, 0.1-2 mm, 0.5-3 mm, 1-2 mm (e.g., approximately 1.5-1.6 mm), 2-5 mm, such as 3 mm, or less. In some examples, the thickness of the electrode can be up to 1 cm. The electrode may have any other suitable thickness (e.g. $1/16^{th}$ inches). The example electrode 700 of FIG. 7 shows flexible sandwiched layers. The flexibility of the electrode 600 can facilitate use for a wide variety of patient types, including pediatric patients, as well as adult patients. For example, the electrode can conform to the patient's body when coupled to the patient as described in relation to FIGS. 9-10. In some examples, the electrode may need to be placed on an intercostal region of the patient, such that the electrode wraps around the side of the patient, to increase the efficacy of the treatment for the patient.

Figure 8:
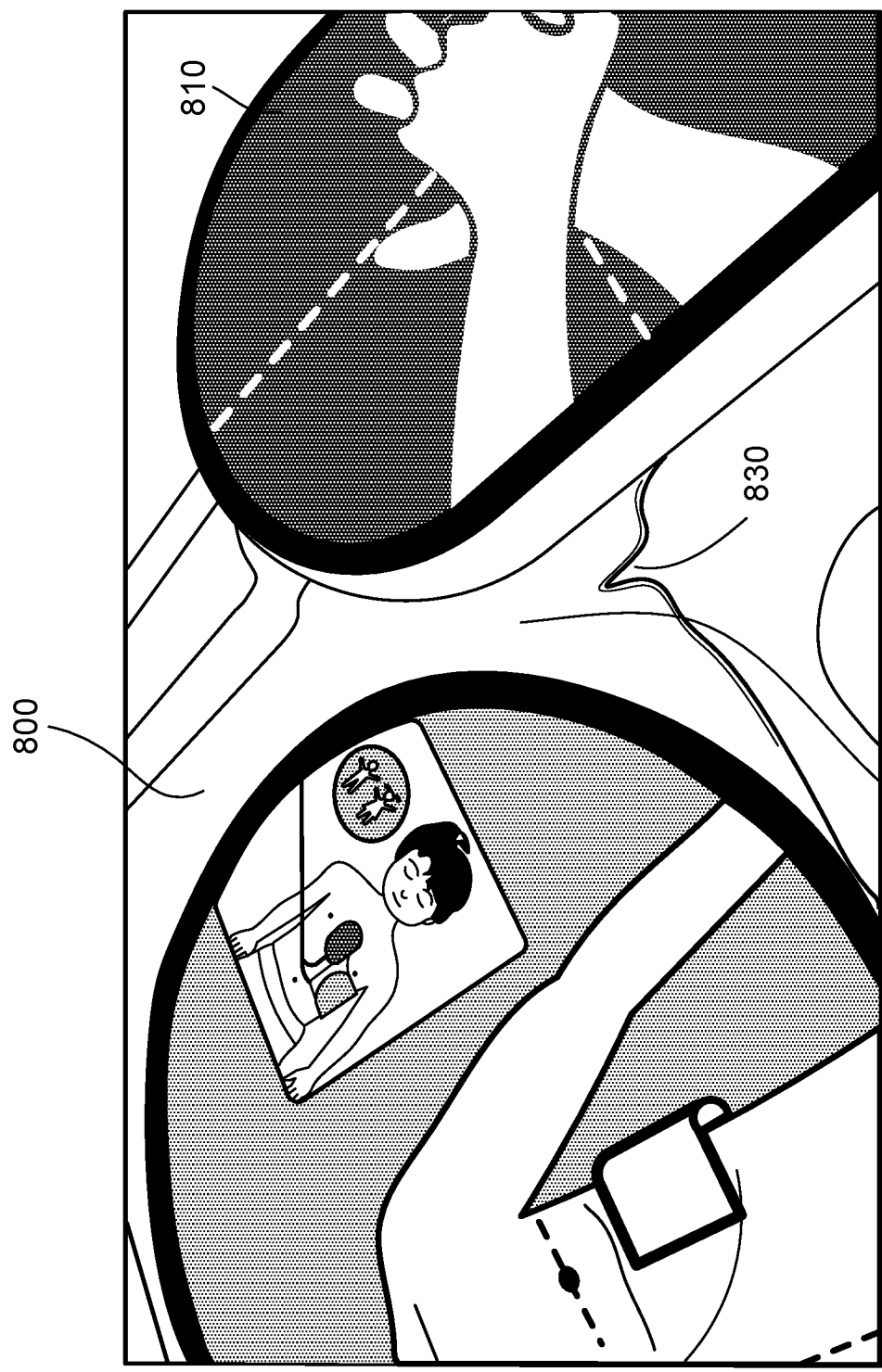
FIG. 8 shows an example of an extension connecting an electrode and a chest compression sensor.

FIG. 8 shows an example of an electrode 800. The electrode can be, for example, the first electrode 110. As described in relation to FIG. 1, the electrode 110 can be attached to a chest compression sensor 130. In FIG. 8, the electrode 800 is attached to the chest compression sensor 810 using an extension 820. The extension 820 can be a protrusion of the upper and bottom surfaces of the electrode 800. The electrode 800 and chest compression sensor 810 have bottom surfaces which can be separated by the extension 820, and each bottom surface can be coated using an adhesive substance as described in relation to FIG. 2 above. The extension 820 can be coated using an adhesive substance (e.g. a pressure-sensitive adhesive). The electrode 800, chest compression sensor 810, and the extension 820 can be stuck to a backing when not in use. The chest compression sensor 810 can be detached from the electrode 800. An optional notch 830 in the extension 820 facilitates intentional tearing or breaking the extension 820 between the chest compression sensor and the electrode 800. Other implementations for facilitating detachment of the electrode from the chest compression sensor may be possible, for example, providing a perforation in the extension. The extension 820 can withstand twisting, warping, and other stresses of use without tearing.

Figure 9:
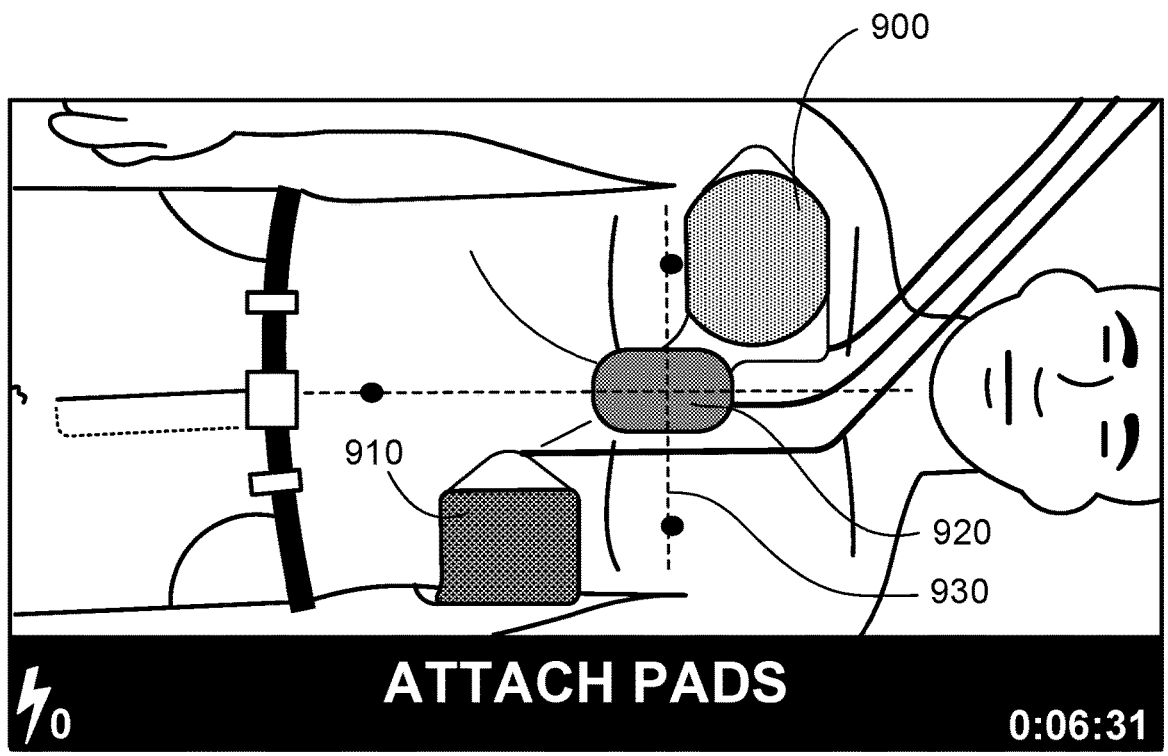
FIG. 9 shows an example of how an electrode assembly may be used for treatment of an adult patient.

FIG. 9 shows an example instruction representing how the electrode assembly 100 may be used for treatment of an adult patient. The patient's bare chest is exposed for placement of the electrode assembly 100. The electrode assembly 100 is removed from the packaging, and the backing of each electrode is removed to expose the adhesive substance (e.g. a conductive hydrogel) on the bottom surface of each electrode, which facilitates adhering of the electrode to the patient body. An electrode 900 is placed on the chest of the patient. For some embodiments, the electrode 900 can be the first electrode 110 of the electrode assembly 100 described in relation to FIG. 1. The electrode 900 can typically be placed on the right side of the adult patient's chest. As discussed herein, the placement of the electrode 900 can be assisted by the placement of an attached chest compression sensor 920. The chest compression sensor 920 can have a pattern, such as a dashed cross, on a upper surface which guides the rescuer for placing the chest compression sensor 920 on the adult patient. The chest compression sensor 920 is typically placed in the approximate center of the adult patient's sternum. The rescuer can orient the pattern on the chest compression sensor 910 with an imaginary cross 930 on the adult patient's chest and body. For example, the user can imagine a line drawn from the adult patient's chin to the adult patient's belly button intersecting with a line drawn across the adult patient's chest to form an approximate cross 930 as seen in FIG. 9. The user can place and orient the CPR sensor 920 such that the center or pattern of the sensor approximately corresponds with the intersecting point of the cross 930. Such placement can correspond with where the user will perform chest compressions on the patient during CPR treatment.

In cases where the electrode 900 is attached to the chest compression sensor 920, the electrode 900 may automatically be oriented to the approximate correct location for treatment on the chest of the adult patient if the chest compression sensor 920 was placed and oriented as described above. In some examples, after the user has properly oriented and positioned the chest compression sensor 920 and electrode 900 on the adult patient's chest, the rescuer can press the chest compression sensor 920 and electrode 900 into the skin of the adult patient so that the adhering substance helps to maintain firm placement of adhesive substances (e.g. a conductive hydrogel or pressure-sensitive adhesive) affix the electrode 900 and chest compression sensor 920. A second electrode 910 is affixed to the adult patient on an intercostal region. As shown in FIG. 9, the electrode 910 is affixed to the lower left intercostal region of the adult patient. Once the electrodes 900 and 910 have been affixed to the adult patient, the patient is ready for treatment. If the rescuer desires feedback on performing chest compressions, the chest compression sensor 920 can be affixed to the patient as described above.

Figure 10:
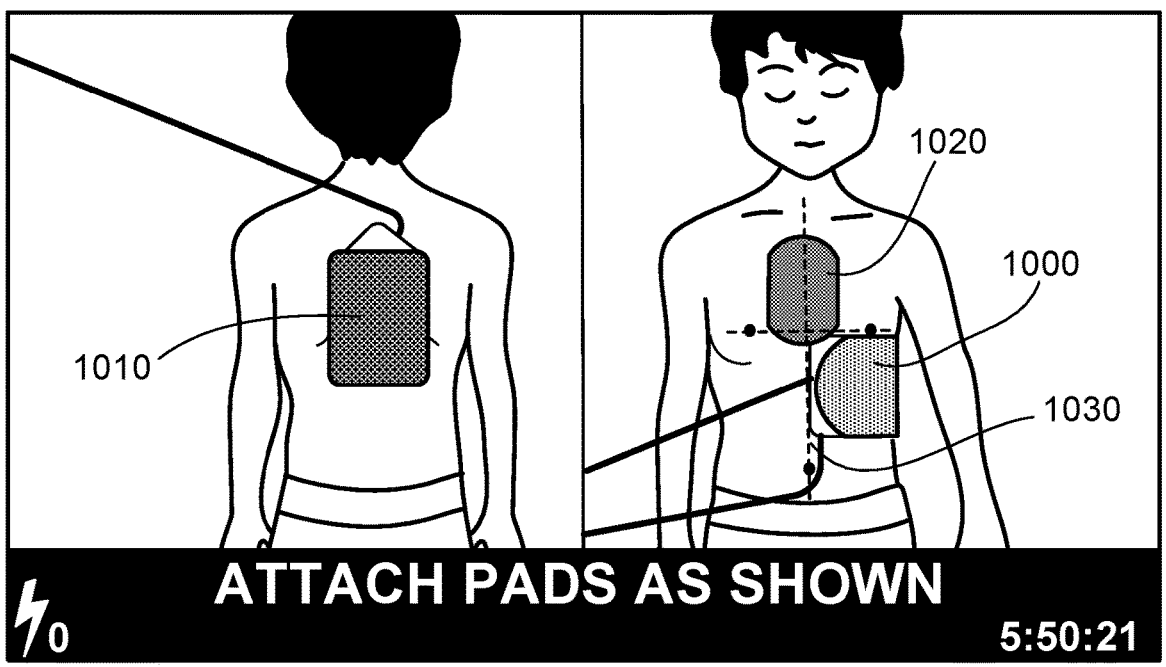
FIG. 10 shows an example of how an electrode assembly may be used for treatment of a pediatric patient.

FIG. 10 shows an example instruction representing how the electrode assembly may be used to treat a pediatric patient. The patient's bare chest can be exposed for placement of the electrode assembly 100. The electrode assembly 100 is removed from packaging and the backing of each electrode is removed to expose the adhering substance (e.g. the conductive hydrogel) on the bottom surface of each electrode.

An electrode 1000 can be placed on an intercostal region of the pediatric patient. The electrode 1000 can be the first electrode 110 of the electrode assembly 100 described in relation to FIG. 1. The electrode 1000 can typically be placed on the left side of the pediatric patient's intercostal region. The placement of the electrode 1000 can be assisted by the placement of an attached chest compression sensor 1020. The chest compression sensor 1020 can have a pattern, such as a dashed cross, on an upper surface which guides the rescuer for placing the chest compression sensor 1020 on the pediatric patient. The chest compression sensor is typically placed in the approximate center of the pediatric patient's sternum. The rescuer can orient the pattern on the chest compression sensor 1010 with an imaginary cross 1030 on the pediatric patient's chest and body. For example, the user can imagine a line drawn from the pediatric patient's chin to the pediatric patient's belly button intersecting with a line drawn across the pediatric patient's chest to form an approximate cross 1030 as seen in FIG. 6. The user can place and orient the CPR sensor 1020 such that the center or pattern of the sensor approximately corresponds with the intersecting point of the cross 1030. Such placement can correspond with where the user will perform chest compressions on the patient during CPR treatment.

In cases where the electrode 1000 is attached to the chest compression sensor 1020, by appropriately positioning the chest compression sensor as described above, the electrode 1000 may be automatically oriented to the approximate correct location for treatment on the lower left intercostal region of the pediatric patient. In some examples, when the chest compression sensor 1020 and electrode 1000 are properly oriented and in the proper locations on the pediatric patient's body, the rescuer can press the chest compression sensor 1020 and electrode 1000 into the skin of the pediatric patient so that adhering substance maintains placement of one or more adhesive substances (e.g. a conductive hydrogel or pressure-sensitive adhesive) affixes the electrode 1000 and chest compression sensor 1020 on the patient's body. A second electrode 1010 is affixed to the pediatric patient on the patient's back. As shown in FIG. 10, the electrode 1010 is affixed to the approximate center of the pediatric patient's back. Once the electrodes 1000 and 1010 have been affixed to the pediatric patient, the patient is ready for treatment. If the rescuer desires feedback on performing chest compressions during CPR, the chest compression sensor 1020 can be affixed to the patient as described above.

Figure 11A:
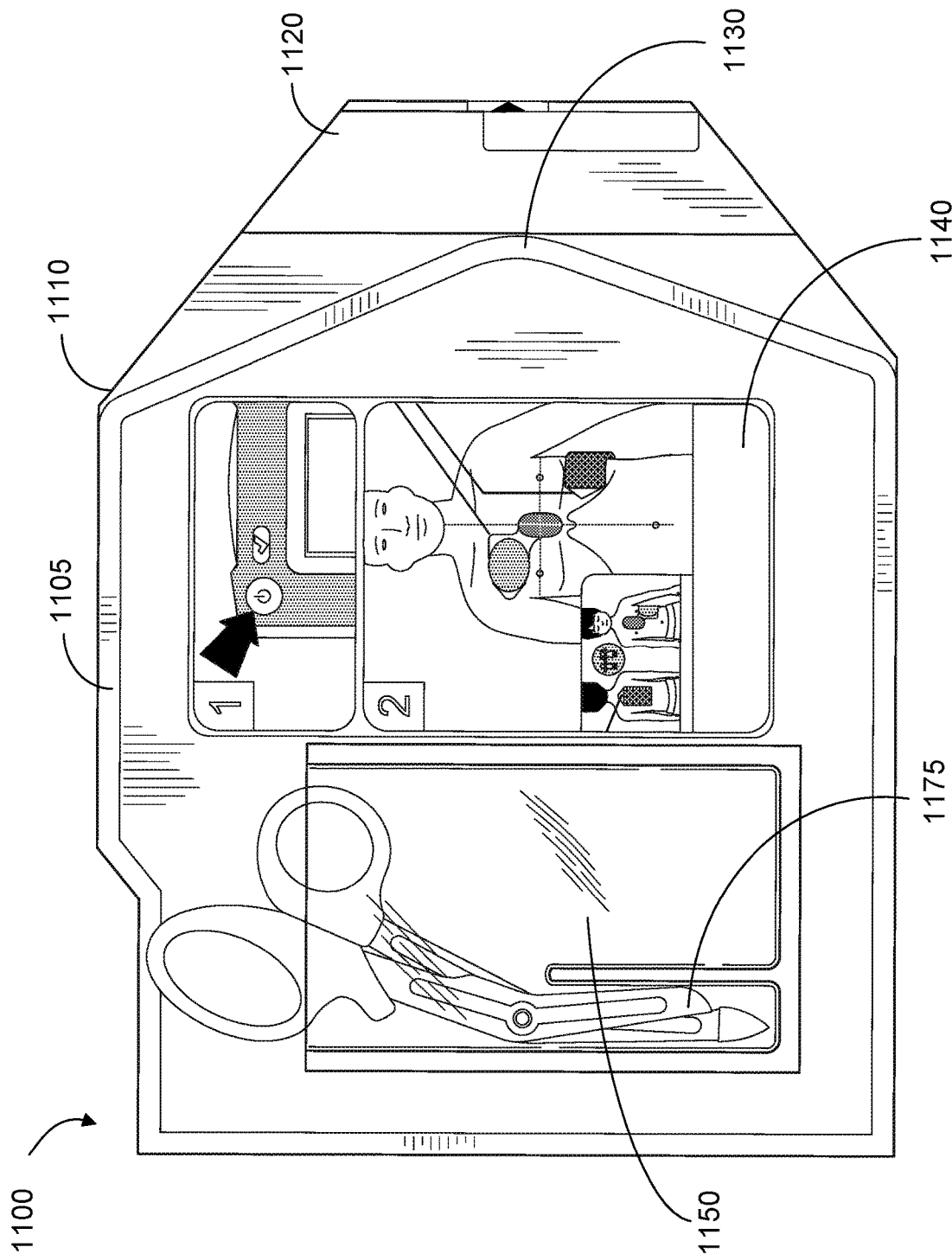
FIGS. 11A-11B show examples of packaging.
Figure 11B:
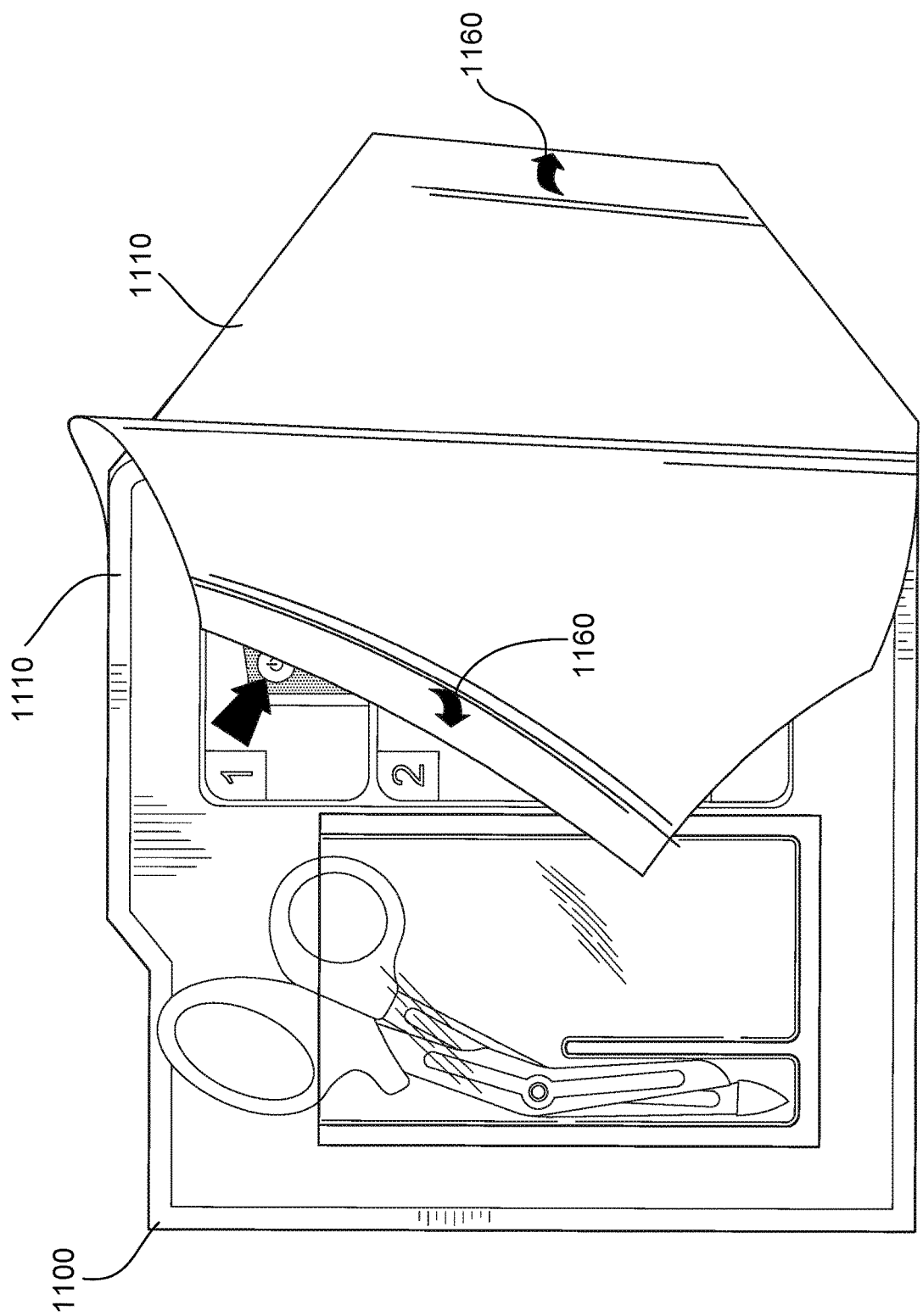

FIGS. 11A-11B show examples of a packaging 1100 for the electrode assembly. The packaging is made of two sheets of material 1110. The two sheets of material are approximately rectangular in shape, though it can be appreciated that other shapes for the packaging are possible. The two sheets of material can be a waterproof plastic. The two sheets may be aligned with respect to one another and affixed to one another with a seal 1105 to form a closed pocket between the sheets. The seal 1105 can be a heat seal. The closed pocket can be airtight so as to preserve the life and usability of the electrode assembly during storage. The seal. The seal 1105 can be near or along three edges of the two sheets. A fourth edge can extend beyond the seal to form a tab 1120 such that the rescuer can grasp the two sheets and pull them apart to access the pocket between the two sheets. The seal along the fourth edge can be angled to facilitate opening the packaging in this manner. In FIGS. 11A-11B for example, the seal forms an angle with a vertex 1130 nearest to the edge of the tab 1120. When the two sheets are pulled apart, the force is concentrated on the vertex of the seal so that the seal opens more easily. Facilitating opening of the packaging may assist the rescuer in an emergency in saving valuable time. Once a part of the seal has been broken, the remaining seal can be easier to break open. The tabs 1120 of the packaging can have indications 1160 indicating to the rescuer where to pull apart the two sheets. In FIG. 11B, for example, the indications 1160 are arrows. The electrode assembly 100 is sealed inside a pocket to increase the longevity of the adhering substance (e.g. the conductive hydrogel) coating the bottom surfaces of the electrodes 110, 120.

In some examples, the packaging 1100 can include a compartment 1150 affixed to the package exterior. The compartment 1150 can be a translucent or transparent pouch. For example, in FIGS. 11A-11B, the compartment 1150 is large enough to contain a pair of scissors 1175. The scissors 1175 can be used by the rescuer to assist in removing the clothing (e.g. shirt, jacket, etc.) of the patient in order to administer treatment with the electrode assembly 100. The compartment 1150 can be affixed to the exterior of the package 1100 and can be transparent or translucent so that the scissors are prominently displayed to the rescuer. Since exposing the chest of the patient is often necessary prior to treatment, the scissors should be used before the electrode assembly. The placement of the scissors in the compartment 1150 assists the rescuer in quickly accessing the scissors in an emergency before accessing the electrode assembly 100. In conventional electrode packaging, scissors for cutting patient clothing are often located deep within the pocket of the packaging, and so the rescuer would oftentimes waste precious time attempting to locate the scissors, or not even notice that the scissors are present and available at all. By placing the scissors in a location that is visually prominent and readily accessible, the rescuer is much more likely to quickly notice the scissors and remove them, and use them for cutting the patient's clothing and subsequently placing the electrode assembly.

In some implementations, the package 1100 can have a label 1140 affixed to the exterior. The label can depict what is inside the package and/or instructions for using the electrode assembly. Any suitable combination of steps may be provided for instructing the rescuer through various phases of the resuscitation process. For example, in FIG. 11A, the label 1140 depicts two steps for using the electrode assembly 100. The first step reminds the rescuer to activate the AED if the rescuer has not already done so. In one example, the rescuer can be instructed to press a power button. The second step may depict instructions for using the electrode assembly 100 on an adult patient. The second step may further depict instructions for using the electrode assembly 100 on a pediatric patient by using an inset containing the pediatric symbol. The instructions for both adult and pediatric use can be consistent with the instructions on the electrodes 110, 120. In some examples, the colors, sizes, and shapes of the electrodes 110, 120 and chest compression sensor 130 match the instructions on the electrodes 110, 120.

It can be appreciated that the packaging and/or electrodes may have any suitable set of instructions provided thereon, in guiding or otherwise assisting the rescuer through the resuscitation process. The label 1140 can include instructions for any step of treatment. For example, instructions for calling emergency services, such as 9-1-1 or EMS can be included. The label can include instructions for opening the package and a depiction of the electrode assembly 100 arranged within the package. The instructions can include steps for operating the AED, such as interfacing the electrode assembly with the AED, powering on the AED, and otherwise using the AED for treatment. The instructions can include steps for performing CPR, such as clearing and checking the airway of the patient, checking a pulse, performing chest compressions, giving breaths, and other steps of CPR for the patient.

The configuration of package 1100 can make the treatment process more intuitive and straightforward for the rescuer, who may be using the electrode assembly for the first time during an emergency. The instructions printed on each piece of the electrode assembly 100 and the packaging 1100 can be consistent in style and thus help guide the rescuer through the treatment process.

What is claimed is:

1. An electrode assembly for use with a defibrillator, the electrode assembly comprising:
   at least one electrode including:
      a dielectric material having:
         a first surface adapted to face toward and be in contact with a chest of either a pediatric patient or an adult patient upon placement of the electrode assembly, and
         a second surface adapted to face away from the pediatric or adult patient upon placement of the electrode assembly and configured to be in contact with a rescuer's hands during chest compressions,
         wherein a majority of the second surface includes pictorial instructions directly printed onto the second surface of the dielectric material and related to use of the electrode assembly; and
         wherein the pictorial instructions related to use of the electrode assembly include a background portion that distinguishes the at least one electrode from another portion of the electrode assembly, the background portion corresponding to a representation of the at least one electrode provided in the pictorial instructions;
   a conductive material in contact with the dielectric material, and a conductive gel in contact with the conductive material, wherein the conductive material and the conductive gel are configured to provide a therapeutic shock to the pediatric or adult patient upon a determination that the patient requires defibrillation, and wherein the dielectric material provides electrical isolation of the rescuer from the conductive material; and
   a chest compression sensor attached to the at least one electrode, the chest compression sensor comprising additional pictorial instructions representing hand placement for the rescuer's hands during the chest compressions,
   wherein the pictorial instructions related to use of the electrode assembly include a first instruction including a representation of the at least one electrode in contact with a surface of an adult patient when in a first orientation, a second instruction including a representation of the at least one electrode in contact with a surface of a pediatric patient when in a second orientation, and a third instruction including a representation of the chest compression sensor comprising the additional pictorial instructions,
   wherein the pictorial instructions related to use of the electrode assembly include a first instruction including a representation of the at least one electrode in contact with a surface of an adult patient when in a first orientation, and a second instruction including a representation of the at least one electrode in contact with a surface of a pediatric patient when in the second orientation, and
   wherein the second instruction includes a pediatric symbol that is separated from and in addition to the representation of the at least one electrode in contact with the surface of the pediatric patient when in the second orientation, the pediatric symbol identifying the representation of the at least one electrode in contact with the surface of the pediatric patient is for pediatric use of the at least one electrode; and
   wherein the second surface of the dielectric material providing electrical isolation of the rescuer from the conductive material comprises a surface-treated polymer including a surface contact angle, for a printable ink, that is below a threshold angle, wherein the majority of the second surface of the dielectric material includes the pictorial instructions that are directly printed, using the printable ink, onto the surface-treated polymer, having the surface contact angle that is below the threshold angle, of the second surface of the dielectric material, the pictorial instructions being related to use of the electrode assembly.

2. The electrode assembly of claim 1 wherein instructions for use with an adult patient are oriented for readability when the electrode assembly is in the first orientation and wherein instructions for use with a pediatric patient are oriented for readability when the electrode assembly is in the second orientation.

3. The electrode assembly of claim 1 wherein the at least one electrode includes a first electrode configured to be placed in contact with the chest of the adult patient when the electrode assembly is in the first orientation, and wherein the first electrode is configured to be placed in contact with an intercostal region of the pediatric patient when the electrode assembly is in the second orientation.

4. The electrode assembly of claim 3 wherein the first electrode is configured to be placed in contact with an upper right chest of the adult patient when the electrode assembly is in the first orientation, and wherein the first electrode is configured to be placed in contact with a lower left intercostal region of the pediatric patient when the electrode assembly is in the second orientation.

5. The electrode assembly of claim 3 wherein the at least one electrode includes a second electrode configured to be placed in contact with a lower left intercostal region of the adult patient when the electrode assembly is in the first orientation, and wherein the second electrode is configured to be placed in contact with a posterior region of the pediatric patient when the electrode assembly is in the second orientation.

6. The electrode assembly of claim 1 wherein the representation of the pediatric patient in the second instruction is oriented between approximately 90 degrees and 180 degrees with respect to the representation of the adult patient in the first instruction.

7. The electrode assembly of claim 1 wherein the background portion is substantially colored to correspond with a color included in the representation of the at least one electrode provided in the pictorial instructions.

8. The electrode assembly of claim 1 wherein substantially all of the second surface comprises the pictorial instructions related to use of the electrode assembly.

9. The electrode assembly of claim 1 wherein the second surface comprises biaxially oriented polypropylene.

10. The electrode assembly of claim 1 wherein the at least one electrode is detachable from the chest compression sensor.

11. The electrode assembly of claim 1 wherein the at least one electrode comprises a removable backing adhered to the first surface, a first portion of the removable backing forming a tab that can be gripped by a user and a second portion of the removable backing adhering to the first surface.

12. The electrode assembly of claim 11 wherein at least one of the removable backing and the first surface includes at least one indicator comprising instructions for removing the backing from the first surface.

13. The electrode assembly of claim 12 wherein the at least one indicator includes a first arrow graphically illustrated on the removable backing and a second arrow graphically illustrated on a second surface of the at least one electrode.

14. The electrode assembly of claim 1 comprising a connector to an electronic port of the defibrillator, the connector terminating an electronic cable, wherein the connector is oriented such that, when connected to the defibrillator, the electronic cable tends to wrap over an edge of the defibrillator.

15. The electrode assembly of claim 1 comprising a connector to an electronic port of the defibrillator, the connector terminating an electronic cable, wherein the electronic cable extends laterally from the connector substantially parallel to a surface of the defibrillator.

16. The electrode assembly of claim 1 comprising a housing for the chest compression sensor, wherein a surface of the housing is marked with a pattern to assist a user in orienting the at least one electrode.

17. The electrode assembly of claim 1 wherein the dielectric material is capable of withstanding voltages of at least 800 V and able to pass a working voltage test according to IEC 601-2-25.

18. The electrode assembly of claim 1 wherein the pictorial instructions have a print resolution of between 50-1500 DPI.

19. The electrode assembly of claim 1 wherein a contact angle of the surface of the dielectric material is between 5-85 degrees.

20. The electrode assembly of claim 1 wherein the conductive material includes at least one of a metallic material and a polymer-based ink.

21. The electrode assembly of claim 1 wherein the pictorial instructions related to use of the electrode assembly including the second instruction including the representation of the at least one electrode in contact with the surface of the pediatric patient when in the second orientation correspond to a defibrillator instruction configured for presentation on an interface of a defibrillator device.

22. The electrode assembly of claim 1 wherein the symbol indicating pediatric use is located inside an inset of the representation of the at least one electrode in contact with a surface of an adult patient, the inset including the second instruction including both the pediatric symbol and the representation of the at least one electrode in contact with the surface of the pediatric patient, the representation being separated from the pediatric symbol inside the inset.

* * * * *